(12) United States Patent
Pochapsky et al.

(10) Patent No.: US 6,596,870 B2
(45) Date of Patent: Jul. 22, 2003

(54) ASYMMETRIC SYNTHETIC METHODS BASED ON PHASE TRANSFER CATALYSIS

(75) Inventors: Thomas C. Pochapsky, Arlington, MA (US); Christine Hofstetter, Fremont, CA (US)

(73) Assignee: Brandeis University, Waltham, MA (US)

( * ) Notice: Subject to any disclaimer, the term of this patent is extended or adjusted under 35 U.S.C. 154(b) by 0 days.

(21) Appl. No.: 09/902,446

(22) Filed: Jul. 10, 2001

(65) Prior Publication Data

US 2002/0115896 A1 Aug. 22, 2002

Related U.S. Application Data

(60) Provisional application No. 60/217,904, filed on Jul. 13, 2000.

(51) Int. Cl.[7] .................... C07D 403/14; C07D 453/04
(52) U.S. Cl. ................... 546/136; 546/134; 546/135; 546/126
(58) Field of Search ............................ 546/136, 135, 546/134, 126

(56) References Cited

U.S. PATENT DOCUMENTS

| | | | |
|---|---|---|---|
| 4,605,761 A | 8/1986 | Dolling | 562/461 |
| 5,126,494 A | 6/1992 | Gilheany et al. | 568/807 |
| 5,175,306 A | 12/1992 | Geiger et al. | 548/452 |
| 5,227,543 A | 7/1993 | Sharpless et al. | 568/860 |
| 5,260,461 A | 11/1993 | Hartung et al. | 549/447 |
| 5,274,177 A | 12/1993 | Ohmori et al. | 560/153 |
| 5,488,131 A | 1/1996 | Myers | 560/3 |
| 5,516,929 A | 5/1996 | Sharpless et al. | 560/38 |
| 5,519,144 A | 5/1996 | Belli et al. | 548/429 |
| 5,521,320 A | 5/1996 | Lee et al. | 548/486 |
| 5,554,753 A | 9/1996 | O'Donnell et al. | 546/134 |
| 5,576,459 A | 11/1996 | Osborn | 562/589 |
| 5,767,304 A | 6/1998 | Sharpless et al. | 560/27 |
| 5,840,915 A | 11/1998 | Lee et al. | 548/486 |
| 5,859,281 A | 1/1999 | Sharpless et al. | 560/12 |
| 5,994,583 A | 11/1999 | Sharpless et al. | 562/575 |

FOREIGN PATENT DOCUMENTS

| | | |
|---|---|---|
| EP | 0 438 796 B1 | 7/1991 |
| EP | 0438 796 A | 7/1991 |
| JP | 06271514 A | 9/1994 |
| JP | 0 6271522 A | 9/1994 |
| JP | 07070121 A | 3/1995 |
| WO | WO 94/27963 | 12/1994 |
| WO | WO 98/22417 | 5/1998 |
| WO | WO 99/42438 | 8/1999 |
| WO | WO 99/55664 | 11/1999 |

OTHER PUBLICATIONS

International Search Report Completed on Jan. 22, 2002 and Mailed on Feb. 1st, 2002.

Hofstetter et al.; "NMR Structure Determination of 1 on Pairs Derived from Quinine: A Model for Templating in Asymmetric Phase–Transfer Reductions by $BH_4^-$ With Implication for Rational Design of Phase–Transfer Catalysts", The Journal of Organic Chemistry, 64(24): 8794–8800, (1999).

Lygo and Wainwright, "A New Class of Asymmetric Phase–Transfer Catalysts Derived fron Cinchona Alkaloids—Applications in the Enantioselective Synthesis of α–Amino Acids", Tetrahedron Letters 38(49): 8595–8598, (1997.

Balcella et al.; "Asymmetric Induction in the Borohydride Reduction of Carbonyl Compounds by Means of a Chiral Phase–Transfer Catalyst", synthesis, pp. 266–267, (Apr. 1976).

Colonna et al.; "Asymmetric Induction in the Borohydride Reduction of Carbonyl Compounds by Means of a Chiral Phase–Transfer Catalyst. Part 2", J.C.S. Perkin I, pp. 371–373, (1978).

Julia et al.; "Phase–Transfer Catalysis Using Chiral Catalysts. Influence of the Structure of the Catalyst on Stereoselectivity. Part 3", J.C.S Perkin I, pp. 574–577, (1981).

*Primary Examiner*—Charanjit S. Aulakh
(74) *Attorney, Agent, or Firm*—Dana M. Gordon; Foley Hoag LLP

(57) ABSTRACT

One aspect of the present invention relates to methods of asymmetric synthesis, e.g., asymmetric hydride reductions of carbonyl groups, using a chiral, non-racemic phase transfer catalyst, a helper nucleophile, and a sterically bulky reagent nucleophile, e.g., an alkoxyhydride derived from a sacrificial ketone and a hydride reagent. Moreover, the sterically bulky reagent nucleophile may be generated in situ or prepared in a prior step. Another aspect of the present invention relates to chiral non-racemic phase transfer catalysts, and their use in the subject methods.

27 Claims, 11 Drawing Sheets

| Catalyst | R | X⁻ |
|---|---|---|
| 1a (NBQCl) | phenyl | Cl⁻ |
| 1b (NBQBH₄) | phenyl | BH₄⁻ |
| 1c (NAQCl) | 9-anthryl | Cl⁻ |

Figure 4

| Helper nucleophile | % ee |
|---|---|
| none | 30 |
| quinine | 34 |
| quinuclidine | 37 |
| 1,4-diazabicyclo[2,2,2]octane | 37 |
| pyridine | 50 |
| thiophene | 26 |
| n-butylsulfide | 33 |
| quinoline | 40 |
| tributylamine | 34 |
| dibutylamine | 40 |
| 4-dimethylaminopyridine (DMAP) | 52 |
| $C_5H_5N:BH_3$ | 0 |
| imidazole | 30 |
| 4- (4-methyl piperidino-pyridine) | 42 |
| pyrrole | 34 |
| pyrimidine | 46 |

Figure 5

| Sacrificial ketone | % ee |
|---|---|
| Benzophenone | 30 |
| Acetophenone | 57 |
| Acetone | 40 |
| 1-Phenyl 2-butanone | 26 |

| R | ee of Product (as a function of substituent and its position) | | |
|---|---|---|---|
| | *ortho* | *meta* | *para* |
| H | 50[b] | 50[b] | 50[b] |
| Acetyl | 72[b] | 78[a] | 64[b] |
| acetoxy | | 20 | |
| methyl | 42 | 44 | 42 |
| Formyl oxime | 39 | 42 | |
| hydroxyl | 34 | 34 | 30 |
| methoxy | | 46 | 46 |
| cyano | | 34 | 36 |
| formyl | | 43 | |
| *tert*-butyl | | | 46 |
| amino | 32 | 32 | 35 |
| bromide | 38 | 42 | |
| -CH(OH)Me | | 30[c] | | a: ice bath; b: ambient temp; c: racemic.

Figure 7

| Ratio of 3-acetyl-pyridine to 9-anthryl trifluoromethyl ketone | ee of Product |
|---|---|
| 1:1 | 36 |
| 2:1 | 41 |
| 50:1 | 72 |
| 100:1 | 58 |

Figure 8

| Reaction time | ee of Product |
|---|---|
| 10 sec | 76 |
| 60 sec | 68 |
| 120 sec | 70 |
| 8 min | 66 |
| 20 min | 64 |

Figure 9

| Temperature (°C) | ee of Product |
|---|---|
| Ambient | 72 |
| 0 | 78 |
| -20 | 82 |
| -54 | 86 |

Figure 10

| Helper Nucleophile(s) | ee of Product |
|---|---|
| None | 30 |
| Pyridine | 50 |
| Acetone | 40 |
| Acetone/Pyridine | 48 |
| Acetophenone | 57 |
| Acetophenone/Pyridine | 64 |
| 2-Acetylpyridine | 72 |
| 3-Acetylpyridine | 78 |
| 4-Acetylpyridine | 64 |

R₁ = anthracenylmethyl

X=Cl

| cation | R₂ | | cation | R₂ |
|---|---|---|---|---|
| 1 N-anthryl quininium | OMe | | 2 N-anthryl quinidinium | OMe |
| 3 N-anthryl cinconidinium | H | | 4 N-anthryl cinchoninium | H |

Q= quinine

ASYMMETRIC SYNTHETIC METHODS BASED ON PHASE TRANSFER CATALYSIS

RELATED APPLICATIONS

This application claims the benefit of priority to U.S. Provisional Patent Application Ser. No. 60/217,904, filed Jul. 13, 2000.

BACKGROUND OF THE INVENTION

Phase Transfer Catalysis

Phase Transfer Catalysis (PTC) technology is used in the commercial manufacture of more than $10 billion of chemicals per year. PTC technology is also used in pollution prevention, pollution treatment and the removal or destruction of impurities in waste and product streams. PTC technology is used in these applications, because it provides many compelling benefits, primarily related to reducing the cost of manufacture of organic chemicals and pollution prevention. Many significant and advantageous process performance achievements are routinely realized by using PTC. Cost reduction and pollution prevention are the two most powerful driving forces in the chemical industry today, and they match precisely the strengths and benefits provided by PTC.

PTC is useful primarily for performing reaction between anions (and certain neutral molecules such as $H_2O_2$ and transition metal complexes such as $RhCl_3$) and organic substrates. PTC is needed because many anions (in the form of their salts, such as NaCN) and neutral compounds are soluble in water and not in organic solvents, whereas the organic reactants are not usually soluble in water. A phase transfer catalyst acts as a shuttling agent by extracting the anion or neutral compound from the aqueous (or solid) phase into the organic reaction phase (or interfacial region) where the anion or neutral compound can freely react with the organic reactant already located in the organic phase. Reactivity is further enhanced, sometimes by orders of magnitude, because once the anion or neutral compound is in the organic phase, it has very little (if any) hydration or solvation associated with it, thereby greatly reducing the energy of activation. Since the catalyst is often a quaternary ammonium salt (e.g., tetrabutyl ammonium, $[C_4H_9]_4N^+$), the ion pair with the counter ion is much looser than say $Na^+X^-$. This looseness of the ion pair is a third key reason for enhanced reactivity, which will ultimately lead to increased productivity (reduced cycle time) in commercial processes. At the end of the reaction, an anionic leaving group is usually generated. This anionic leaving group is conveniently brought to the aqueous (or solid) phase by the shuttling catalyst, thus facilitating the separation of the waste material from the product. This mechanism is often called the "extraction mechanism" of phase-transfer catalysis.

The extraction mechanism accounts for many of the benefits of PTC, including: achieving high reactivity (reactants are in the same phase with less hydration in an ion pair); flexibility in choosing or eliminating solvent (a properly chosen quaternary ammonium catalyst can extract almost any anion into almost any organic medium, including into the product or into one of the organic reactants resulting in a solvent-free process); reducing the excess of water-sensitive reactants (such as phosgene, benzoyl chloride, esters and dimethyl sulfate since they are protected in the bulk organic phase from the aqueous phase by interfacial tension); higher selectivity (lower energy of activation allows reduction of reaction temperature and time); the use of inexpensive and less hazardous bases (hydroxide is easily transferred and activated in nearly all organic solvents) and many other benefits.

PTC delivers high productivity, enhanced environmental performance, improved safety, better quality and increased plant operability in hundreds of commercial manufacturing processes for organic chemicals in dozens of reaction categories. PTC provides high performance in real world applications, primarily in reducing cost of manufacture and pollution prevention. Enormous opportunity exists right now to increase corporate profits and process performance by retrofitting existing non-PTC processes with PTC and by developing new processes using PTC. Companies can achieve higher performance using PTC by developing these processes.

Asymmetric Synthesis Using Phase Transfer Catalysis

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. The advantages associated with enantiomerically pure compounds often include fewer side effects and greater potency. See, e.g., Stinson, S. C., *Chem Eng News,* Sep. 28, 1992, pp. 46–79.

Traditional methods of organic synthesis were often optimized for the production of racemic materials. The production of enantiomerically pure material has historically been achieved in one of two ways: (a) the use of enantiomerically pure starting materials derived from natural sources (the so-called "chiral pool"); and (b) the resolution of racemic mixtures by classical techniques. Each of these methods has serious drawbacks, however. The chiral pool is limited to compounds found in nature, so only certain structures and configurations are readily available. Resolution of racemates, which requires the use of resolving agents, may be inconvenient and time-consuming. Furthermore, resolution often means that the undesired enantiomer is discarded, thus decreasing efficiency and wasting half of the material.

Taken together, the many advantages of PTC and the increasing importance of ready access to enantiomerically-enriched and/or enantiomerically-pure compounds and intermediates make desirable methods of phase transfer catalysis which induce asymmetry into product molecules.

SUMMARY OF THE INVENTION

One aspect of the present invention relates to methods of asymmetric synthesis, e.g., asymmetric hydride reductions of carbonyl groups, using a chiral, non-racemic phase transfer catalyst, a helper nucleophile, and a sterically bulky reagent nucleophile, e.g., an alkoxyhydride derived from a sacrificial ketone and a hydride reagent. Moreover, the sterically bulky reagent nucleophile may be generated in situ or prepared in a prior step. Another aspect of the present invention relates to chiral non-racemic phase transfer catalysts, and their use in the subject methods.

BRIEF DESCRIPTION OF THE DRAWINGS

FIG. 4 tabulates the enantiomeric excesses observed in the reduction of 9-anthryl trifluoromethyl ketone by $NaBH_4$ with N-anthryl quininium chloride as a catalyst and an excess of a helper nucleophile, as a function of the helper nucleophile.

FIG. 5 tabulates the enantiomeric excesses observed in the reduction of 9-anthryl trifluoromethyl ketone by $NaBH_4$ with N-anthryl quininium chloride as a catalyst and an excess of a sacrificial ketone, as a function of the sacrificial ketone used.

FIG. 7 tabulates the enantiomeic excesses observed using various ratios of helper nucleophile (3-acetylpyridine) to 9-anthryl trifluoromethyl ketone in the borohydride reduction of the latter. The amount of catalyst ($8 \times 10^{-6}$ mol) and 3-acetyl pyridine ($4 \times 10^{-4}$ mol) were held constant, while the amount of 9-anthryl trifluoromethyl ketone was varied. The total volume of solution (3 mL) was held constant, and the reactions were run at ambient temperature.

FIG. 8 tabulates the enantiomeric excess observed in the borohydride reduction of 9-anthryl trifluoromethyl ketone as a function of reaction time. The reactions were run with fifty equivalents of 3-acetylpyridine and one equivalent of 9-anthryl trifluoromethyl ketone, using 10 mol % of N-anthryl quininium chloride. Aliquots (about 5 drops) were removed from the reaction mixture at the indicated times, and run through a Pasteur pipette containing dry alumina to quench the reaction. The pipette was then flushed with chloroform to collect the product alcohol. The reactions were run at ambient temperature.

FIG. 9 tabulates the enantiomeric excess observed in the borohydride reduction of 9-anthryl trifluoromethyl ketone as a function of temperature, using 3-acetylpyridine as the helper nucleophile. The reactions were run with fifty equivalents of 3-acetylpyridine to one equivalent of 9-anthryl trifluoromethyl ketone, using 10 mol % of N-anthracenylmethyl quininium chloride as catalyst. The aqueous phase contained 4 mmol of $NaBH_4$ dissolved in about 5 mL of distilled $H_2O$. The total volume of the organic layer was 3 mL.

FIG. 10 tabulates the enantiomeric excess observed in the borohydride reduction of 9-anthryl trifluoromethyl ketone as a function of the helper nucleophile(s) used. The reactions were run at ambient temperature. The organic layer consisted of 0.08 mmol 9-anthryl trifluoromethyl ketone, 4 mmol helper nucleophile, and 0.008 mmol catalyst in 3 mL $CHCl_3$. The mixtures were stirred rapidly with 2–3 mL distilled water with $NaBH_4$. In reactions using two helper nucleophiles, 4 mmol of each helper was used.

DETAILED DESCRIPTION OF THE INVENTION

Figure 1:
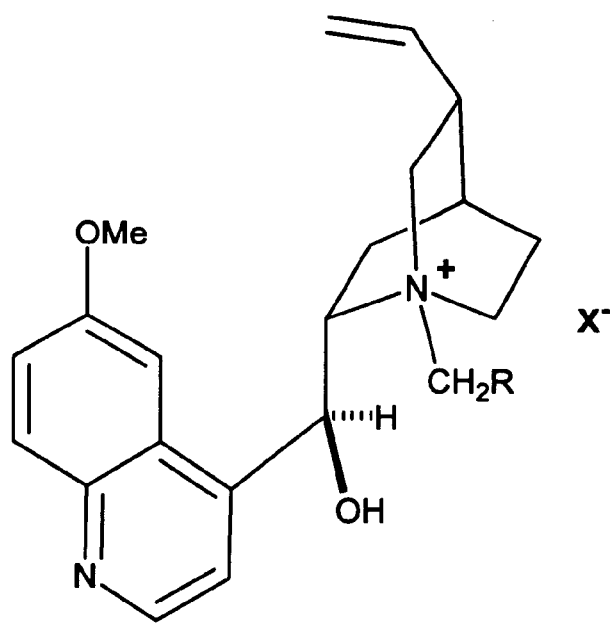
FIG. 1 depicts the structures of phase transfer catalysts 1a–1c, referred to in Example 1.

The ability to selectively transform a prochiral center in a compound to an enantiomerically enriched or enantiomerically pure chiral center has broad application, especially in the agricultural, pharmaceutical, and polymer industries. As described herein, the present invention relates to catalysts and methods for the catalytic asymmetric transformation of a prochiral center in a compound to an enantiomerically enriched or enantiomerically pure chiral center. The catalysts of the present invention are chiral, non-racemic compounds that function as phase transfer catalysts in certain asymmetric synthetic organic transformations. The primary elements of the methods of the present invention, which are set forth in greater detail below, are: (a) a non-racemic, chiral phase transfer catalyst; (b) a compound comprising a prochiral center, e.g., the carbon of a carbon-heteroatom π-bond; (c) a helper nucleophile, e.g., a substituted pyridine; and (d) a sterically bulky reagent nucleophile, which under the reaction conditions stereoselectively attacks the prochiral center, generating an enantiomerically enriched or enantiomerically pure chiral center.

Further, the asymmetry of the chiral non-racemic phase transfer catalyst combines with the steric bulk of the reagent nucleophile to give enhanced stereoselectivity in the methods of the present invention. Moreover, the sterically bulky reagent nucleophile may be generated in situ or prepared in a prior step. Additionally, the catalysts and methods of the present invention can be exploited to effect kinetic resolutions of racemic and diastereomeric mixtures and the like.

Furthermore, the addition of neutral nucleophiles to phase transfer reactions involving chiral non-racemic cationic phase transfer catalysts, an anionic sterically-bulky reagent nucleophile, and a neutral prochiral unsaturated substrate gives increased enantiomeric excesses in the product of the reaction relative to enantiomeric excess in the absence of the neutral nucleophile. This modification has been shown to applicable to the reduction of a prochiral ketone by $NaBH_4$, but should also be applicable to other nucleophilic additions under phase transfer conditions such as reductive amination by $NaCNBH_3$, amino nitrile formation (Strecker amino acid synthesis), Michael additions, nitrite additions; in short, virtually any nucleophilic addition that has been catalyzed under phase transfer conditions.

The possible types of neutral helper nucleophile added are almost limitless, and would be optimized for any given situation. The only limitation is the requirement that there be no acidic hydrogen directly bonded to the nucleophilic center, so that the addition of the nucleophile to the site of unsaturation in the neutral substrate is reversible (Scheme A).

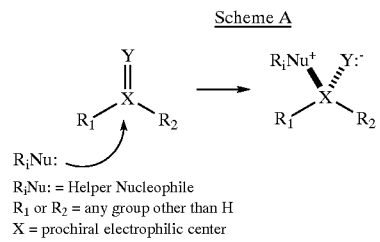

Scheme A $R_iNu:$ $R_iNu:$ = Helper Nucleophile
$R_1$ or $R_2$ = any group other than H
X = prochiral electrophilic center Scheme A shows a generalized model for how the helper nucleophile might form a transient zwitterionic complex with the neutral unsaturated substrate at the prochiral center (usually carbon). This complex, by virtue of the negative charge on Y, interacts more strongly with the cationic chiral phase transfer catalyst than the neutral substrate would in the absence of the helper nucleophile. Since the helper nucleophile need not be chiral, equal amounts of both enantiomers of the zwitterionic intermediate are formed. The complexes formed with the cationic catalyst will be diastereomeric, with different rates of reaction with the reagent anion nucleophile. The final product results from the directed addition of the reagent anion nucleophile to the zwitterionic intermediate, with displacement of the helper nucleophile, regenerating the helper and giving a chiral product (which will be neutralized by solvent protons). Scheme B (below) shows the generation of the preferred chiral product from one diastereomeric complex.

Scheme B

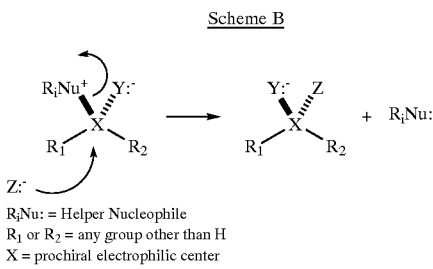

Figure 2:
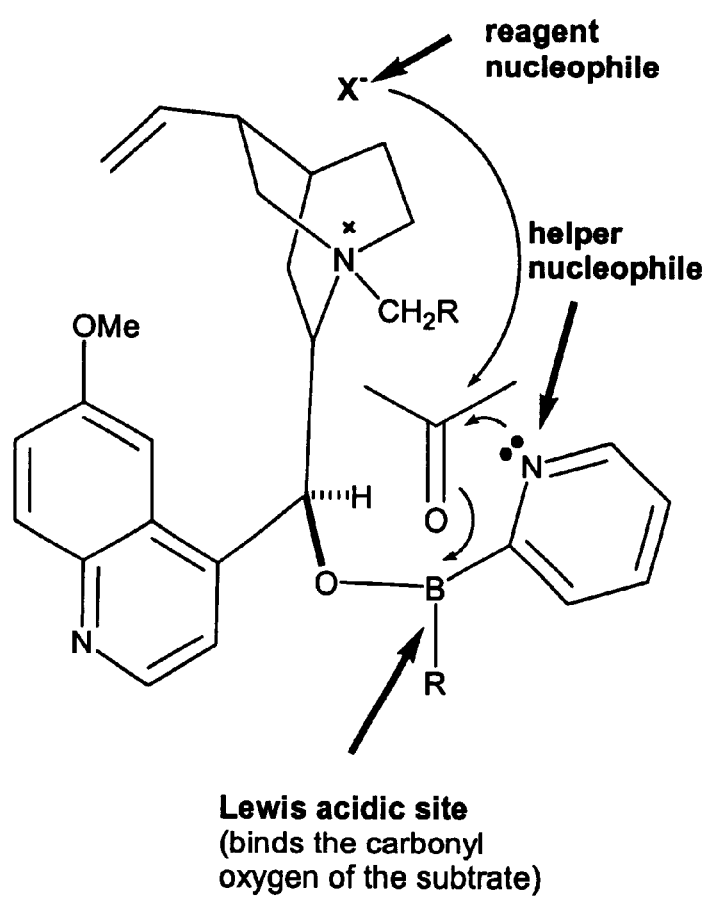
FIG. 2 depicts a chiral non-racemic catalyst derived from quinine, and a mechanistic rationale for enantioselectivity of the methods of the present invention based on said catalyst.

$R_iNu:$ = Helper Nucleophile
$R_1$ or $R_2$ = any group other than H
X = prochiral electrophilic center The role of the chiral non-racemic cationic catalyst has been filled by many different compounds, most commonly quaternary ammonium salts derived from cinchona alkaloids. Other chiral non-racemic cationic catalysts have been tested, most notably ephedrine derivatives. The impact of the helper nucleophile on asymmetric PTC reactions should not be dependent on the particular chiral catalyst used, so long as it is cationic. Another contemplated refinement of this methodology is to incorporate the helper nucleophile into the catalyst, forming a "cleft", which would likely yield even better enantiomeric excesses because only one enantiomer of the zwitterionic intermediate is likely to form. See FIG. 2.

The use of sterically bulky anionic reagent nucleophiles, e.g., reducing agents, in phase transfer reactions that generate chiral products produces improved enantiomeric excess in the products relative to less-hindered anionic reagents. This result has been demonstrated by in situ generation of sterically hindered alkoxyborohydrides from sacrificial ketones in the phase transfer reduction of prochiral ketones, but will likely be applicable with a wide range of generated bulky anionic reagents.

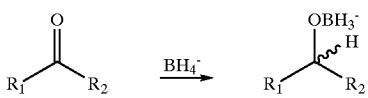

Figure 3:
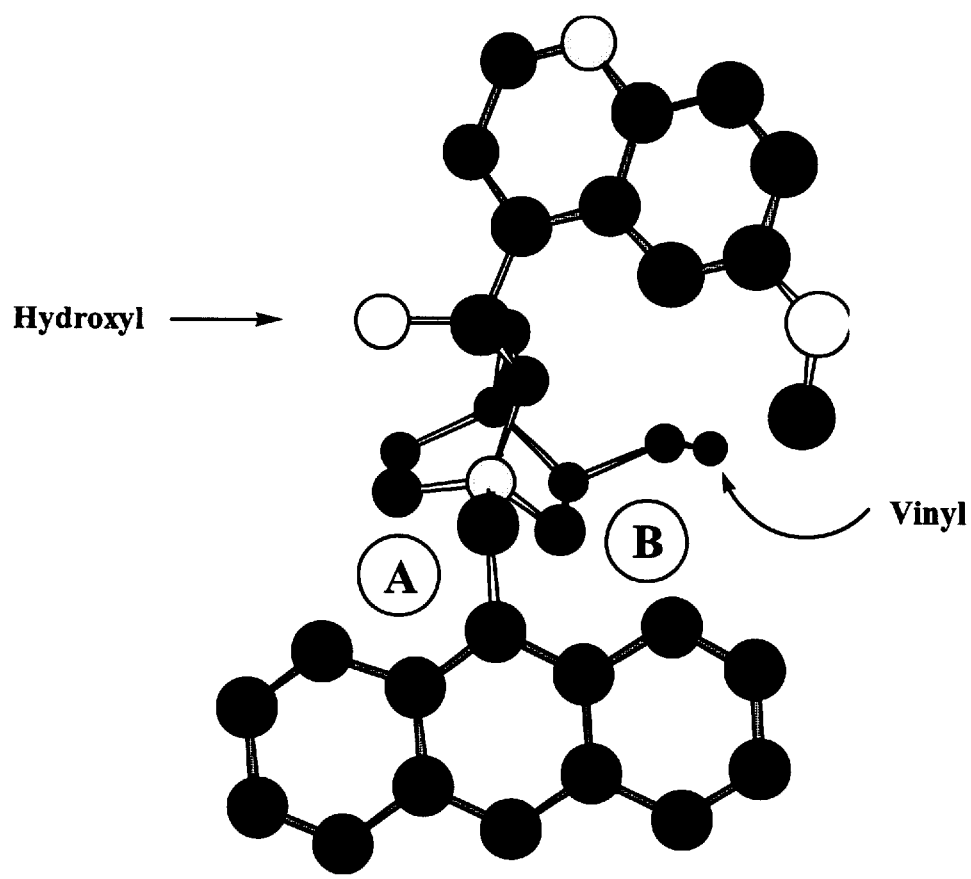
FIG. 3 depicts the structure of the NAQ+ cation, including the anionic binding sites, as determined from observed interionic NOEs. The site labeled A is occupied by both $BF_4^-$ and $BH_4^-$; the site labeled B is occupied by $BH_4^-$, but at least partially blocked to $BF_4^-$. Protons are omitted for clarity. The positions of the vinyl and hydroxyl substituents are indicated with arrows.

The origin of this effect likely lies in discriminatory binding of the reagent anion to the chiral catalyst cation. It has been shown that two sites are available for reagent anion binding on the chiral catalyst cation used in the model reaction. See Hofstetter, C. et al. *J. Org. Chem.* 1999, 64, 8794–8800. Only one binding mode is expected to result in asymmetric reduction of substrate ketone, and steric discrimination by the catalyst between the binding sites results in the observed enhanced enantiomeric excess in the products. See id. By making the anion sterically bulkier, this discrimination becomes greater, thereby improving the enantiomeric excess of the product. See FIG. 3.

Definitions

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as water, amines, mercaptans and alcohols, and charged moieties such as alkoxides, thiolates, carbanions, and a variety of organic and inorganic anions. Illustrative anionic nucleophiles include simple anions such as hydroxide, azide, cyanide, thiocyanate, acetate, formate or chloroformate, and bisulfite. Organometallic reagents such as organocuprates, organozincs, organolithiums, Grignard reagents, enolates, acetylides, and the like may, under appropriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g. tosylates), chlorides, bromides, iodides, and the like The terms "electrophilic atom", "electrophilic center" and "reactive center" as used herein refer to the atom of the substrate which is attacked by, and forms a new bond to, the nucleophile. For example, the atom from which a leaving group departs, the carbon of a carbonyl group, or a carbon of a carbon-carbon multiple bond.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The terms "Lewis base" and "Lewis basic" are recognized in the art, and refer to a chemical moiety capable of donating a pair of electrons under certain reaction conditions. Examples of Lewis basic moieties include uncharged compounds such as alcohols, thiols, olefins, and amines, and charged moieties such as alkoxides, thiolates, carbanions, and a variety of other organic anions.

The terms "Lewis acid" and "Lewis acidic" are art-recognized and refer to chemical moieties which can accept a pair of electrons from a Lewis base.

The term "meso compound" is recognized in the art and means a chemical compound which has at least two chiral centers but is achiral due to an internal plane, or point, of symmetry.

The term "chiral" refers to molecules which have the property of non-superimposability on their mirror image partner, while the term "achiral" refers to molecules which are superimposable on their mirror image partner. A "prochiral molecule" is an achiral molecule which has the potential to be converted to a chiral molecule in a particular process. Likewise, a "prochiral center" is an achiral atom in a molecule which has the potential to be converted to a chiral center in a particular process.

The term "stereoisomers" refers to compounds which have identical chemical constitution, but differ with regard to the arrangement of their atoms or groups in space. In particular, the term "enantiomers" refers to two stereoisomers of a compound which are non-superimposable mirror images of one another. The term "diastereomers", on the other hand, refers to the relationship between a pair of stereoisomers that comprise two or more asymmetric centers and are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an e.e. for a particular enantiomer that is larger than the e.e. of the reaction lacking the chiral catalyst.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant preponderance of a certain regioisomer.

The term "reaction product" means a compound which results from the reaction of a nucleophile and a substrate. In general, the term "reaction product" will be used herein to refer to a stable, isolable compound, and not to unstable intermediates or transition states.

The term "substrate" is intended to mean a chemical compound which can react with a nucleophile, or with a ring-expansion reagent, according to the present invention, to yield at least one product having a stereogenic center.

The term "catalytic amount" is recognized in the art and means a substoichiometric amount relative to a reactant. As used herein, a catalytic amount means from 0.0001 to 90 mole percent relative to a reactant, more preferably from 0.001 to 50 mole percent, still more preferably from 0.01 to 10 mole percent, and even more preferably from 0.1 to 5 mole percent relative to a reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

% enantiomeric excess $A$ $(ee)$=(% enantiomer $A$)−(% enantiomer $B$)

where A and B are the enantiomers formed. Additional terms that are used in conjunction with enatioselectivity include "optical purity" or "optical activity". An enantioselective reaction yields a product with an e.e. greater than zero. Preferred enantioselective reactions yield a product with an e.e. greater than 20%, more preferably greater than 50%, even more preferably greater than 70%, and most preferably greater than 80%.

A diastereoselective reaction converts a chiral reactant (which may be racemic or enantiomerically pure) to a product enriched in one diastereomer. If the chiral reactant is racemic, in the presence of a chiral non-racemic reagent or catalyst, one reactant enantiomer may react more slowly than the other. This class of reaction is termed a kinetic resolution, wherein the reactant enantiomers are resolved by differential reaction rate to yield both enantiomerically-enriched product and enantimerically-enriched unreacted substrate. Kinetic resolution is usually achieved by the use of sufficient reagent to react with only one reactant enantiomer (i.e. one-half mole of reagent per mole of racemic substrate). Examples of catalytic reactions which have been used for kinetic resolution of racemic reactants include the Sharpless epoxidation and the Noyori hydrogenation.

A regioselective reaction is a reaction that occurs preferentially at one reactive center rather than another non-identical reactive center. For example, a regioselective reaction of an unsymmetrically substituted epoxide substrate would involve preferential reaction at one of the two epoxide ring carbons.

The term "non-racemic" with respect to the chiral catalyst, means a preparation of catalyst having greater than 50% of a given enantiomer, more preferably at least 75%. "Substantially non-racemic" refers to preparations of the catalyst which have greater than 90% ee for a given enantiomer of the catalyst, more preferably greater than 95% ee.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 of fewer. Likewise, preferred cycloalkyls have from 4–10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl, an alkoxyl, and ester, a phosphoryl, an amine, an amide, an imine, a thiol, a thioether, a thioester, a sulfonyl, an amino, a nitro, or an organometallic moiety. It will be understood by those skilled in the art that the moieties substituted on the hydrocarbon chain can themselves be substituted, if appropriate. For instance, the substituents of a substituted alkyl may include substituted and unsubstituted forms of amines, imines, amides, phosphoryls (including phosphonates and phosphines), sulfonyls (including sulfates and sulfonates), and silyl groups, as well as ethers, thioethers, selenoethers, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, thioalkyls, aminoalkyls, carbonyl-substituted alkyls, $CF_3$, CN, and the like.

The terms "alkenyl" and "alkynyl" refer to unsaturated aliphatic groups analogous in length and possible substitution to the alkyls described above, but which contain at least one double or triple carbon-carbon bond, respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

As used herein, the term "amino" means —$NH_2$; the term "nitro" means —$NO_2$; the term "halogen" designates —F, —Cl, —Br or —I; the term "thiol" means —SH; the term "hydroxyl" means —OH; the term "sulfonyl" means —SO$_2$—; and the term "organometallic" refers to a metallic atom (such as mercury, zinc, lead, magnesium or lithium) or a metalloid (such as silicon, arsenic or selenium) which is bonded directly to a carbon atom, such as a diphenylmethylsilyl group.

Thus, the term "alkylamine" as used herein means an alkyl group, as defined above, having a substituted or unsubstituted amine attached thereto. In exemplary embodiments, an "amine" can be represented by the general formula:

wherein R$_8$ and R$_9$ each independently represent a hydrogen, an alkyl, an alkenyl, —(CH$_2$)$_m$—R$_7$, —C(=O) alkyl, —C(=O)-alkenyl, —C(=O)-alkynyl, —C(=O)—(CH$_2$)$_m$—R$_7$, or R$_8$ and R$_9$ take with the N atom to which they are attached complete a heterocycle having from 4 to 8 atoms in the ring structure; R$_7$ represents an aryl, a cycloalkyl, a cycloalkenyl, a heterocycle or a polycycle; and m is zero or an integer in the range of 1 to 8.

Likewise, the term "alkylamide" refers to an alkyl group having a substituted or unsubstituted amide group attached thereto. For instance, an "amide" can be represented by the general formula:

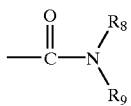

wherein R$_8$ and R$_9$ are as defined above.

The term "alkylimine" refers to an alkyl group having a substituted or unsubstituted imine attached thereto. An "imine" can be represented by the general formula:

wherein R$_8$ is as described above.

The term "thioalkyl" refers to an alkyl group, as defined above, having a sulfhydryl or thioether group attached thereto. In preferred embodiments, the "thioether" moiety is represented by one of —S-alkyl, —S-alkenyl, —S-alkynyl, and —S—(CH$_2$)$_m$—R$_7$, wherein m and R$_7$ are defined above.

The term "carbonyl-substituted alkyl" as used herein means an alkyl group, as defined above, having a substituted or unsubstituted carbonyl group attached thereto, and includes aldehydes, ketones, carboxylates and esters. In exemplary embodiments, the "carbonyl" moiety is represented by the general formula:

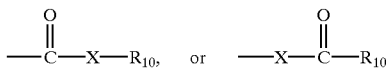

wherein X is absent or represents an oxygen or a sulfur, and R$_{10}$ represents a hydrogen, an alkyl, an alkenyl, or —(CH$_2$)$_m$—R$_7$, where m and R$_7$ are as defined above. Where X is an oxygen, the formula represents an "ester".

Where X is a sulfur, the formula represents a "thioester." Where X is absent, and R$_{10}$ is not hydrogen, the above formula represents a "ketone" group. Where the oxygen atom of the above formula is replaced by sulfur, the formula represents a "thiocarbonyl" group.

The terms "alkoxyl" or "alkoxy" as used herein refer to an alkyl group, as defined above, having an oxygen radical attached thereto. Representative alkoxyl groups include methoxy, ethoxy, propoxy, tert-butoxy and the like. An "ether" is two hydrocarbons covalently linked by an oxygen. Accordingly, the substituent of an alkyl which renders that alkyl an ether is or resembles an alkoxyl, such as can be represented by one of —O—alkyl, —O-alkenyl, —O-alkynyl, —O-(CH$_2$)$_m$—R$_7$, where m and R$_7$ are described above.

Thus, the term "phosphorylalkyl" as used herein means an alkyl group, as defined above, having a substituted or unsubstituted phosphoryl group attached thereto. A "phosphoryl" can in general be represented by the formula:

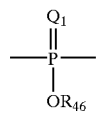

wherein Q$_1$ represented S or O, and R$_{46}$ represents hydrogen, a lower alkyl or an aryl. When used to substitute an alkyl, the phosphoryl group of the phosphorylalkyl can be represented by the general formula:

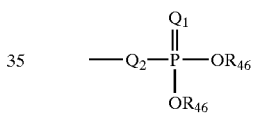

wherein Q$_1$ represented S or O, and each R$_{46}$ independently represents hydrogen, a lower alkyl or an aryl, Q$_2$ represents O, S or N.

The term "metalloalkyl" refers to an alkyl group, as defined above, having a substituted or unsubstituted organometallic group attached thereto. A "silyl alkyl" is an alkyl having a substituted silicon attached thereto. In a preferred embodiment, the "silyl" moiety which may be substituted on the alkyl can be represented by the general formula:

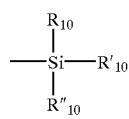

wherein R$_{10}$, R'$_{10}$ and R"$_{10}$ independently represent a hydrogen, an alkyl, an alkenyl, or —(CH$_2$)$_m$—R$_7$, m and R$_7$ being defined above.

Likewise, a "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se-(CH$_2$)$_m$—R$_7$, m and R$_7$ being defined above.

The term "sulfonyl" as used herein means a S(O)$_2$ moiety bonded to two carbon atoms. Thus, in a preferred embodiment, a sulfone has the following structure:

wherein the single bonds are between carbon and sulfur.

The term "sulfonate" as used herein means a sulfonyl group, as defined above, attached to a hydroxyl, alkyloxy or aryloxy group. Thus, in a preferred embodiment, a sulfonate has the structure:

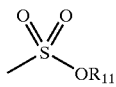

in which $R_{11}$ is absent, hydrogen, alkyl, or aryl.

The term "sulfate", as used herein, means a sulfonyl group, as defined above, attached to two hydroxy or alkoxy groups. Thus, in a preferred embodiment, a sulfate has the structure:

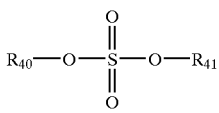

in which $R_{40}$ and $R_{41}$ are independently absent, a hydrogen, an alkyl, or an aryl. Furthermore, $R_{40}$ and $R_{41}$, taken together with the sulfonyl group and the oxygen atoms to which they are attached, may form a ring structure having from 5 to 10 members.

Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6- and 7-membered single-ring aromatic groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycle". The aromatic ring can be substituted at one or more ring positions with such substituents as described above, as for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —$CN$, or the like.

The terms "heterocycle" or "heterocyclic group" refer to 4 to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —$CN$, or the like.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —$CN$, or the like.

The term "heteroatom" as used herein means an atom of any element other than carbon or hydrogen. Preferred heteroatoms are nitrogen, oxygen, sulfur, phosphorus and selenium.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The terms ortho, meta and para apply to 1,2-, 1,3- and 1,4-disubstituted benzenes, respectively. For example, the names 1,2-dimethylbenzene and ortho-dimethylbenzene are synonymous.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms, represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry;* this list is typically presented in a table entitled *Standard List of Abbreviations.* The abbreviations contained in said list, and all abbreviations utilized by organic chemists of ordinary skill in the art are hereby incorporated by reference.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis,* $2^{nd}$ ed.; Wiley: New York, 1991).

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Catalysts of the Invention

The catalysts employed in the subject methods are non-racemic chiral quaternary ammonium ions, i.e., nitrogen bonded to four carbons, which present an asymmetric environment, causing differentiation between the two enantiotopic faces of a prochiral carbon, e.g., the carbon atom of a carbon-heteroatom π-bond. In general, catalysts used in or contemplated by the present invention can be characterized in terms of a number of features. For instance, a salient aspect of each of the catalysts contemplated by the instant invention concerns the use of asymmetric bicyclic or polycyclic scaffolds incorporating the quaternary ammonium moiety providing a rigid or semi-rigid environment. This feature, through imposition of structural rigidity on the catalyst, in combination with its one or more asymmetric centers, contributes to the creation of a meaningful difference in the energies of the corresponding diastereomeric transitions states for the overall transformation. Furthermore, the choice of substituents may also effect catalyst reactivity; typically, bulkier substituents are found to provide higher catalyst turnover numbers and enhanced enantioselectivities.

A preferred embodiment for each of the embodiments described above provides a catalyst having a molecular weight less than 2,000 g/mol, more preferably less than 1,000 g/mol, and even more preferably less than 500 g/mol. Additionally, the substituents on the catalyst can be selected to influence the various properties of the catalyst. For example, the catalyst's substituents can effect the electronic properties of the catalyst. Choice of appropriate substituents thus makes possible the "tuning" of the reaction rate and the stereoselectivity of the reaction.

In certain embodiments, the catalyst of the present invention is a compound represented by structure 3:

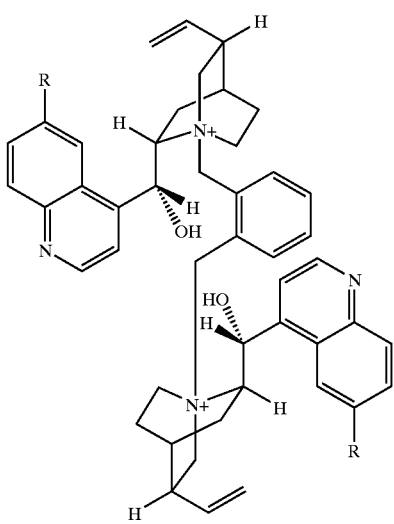

wherein
R represents independently for each occurrence hydroxyl, alkoxyl, or aryloxyl.

In certain embodiments, the catalyst of the present invention is a compound represented by structure 4:

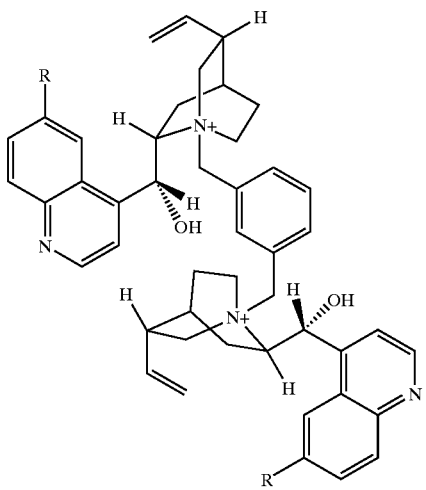

wherein
R represents independently for each occurrence hydroxyl, alkoxyl, or aryloxyl.

In certain embodiments, the catalyst of the present invention is a compound represented by structure 5:

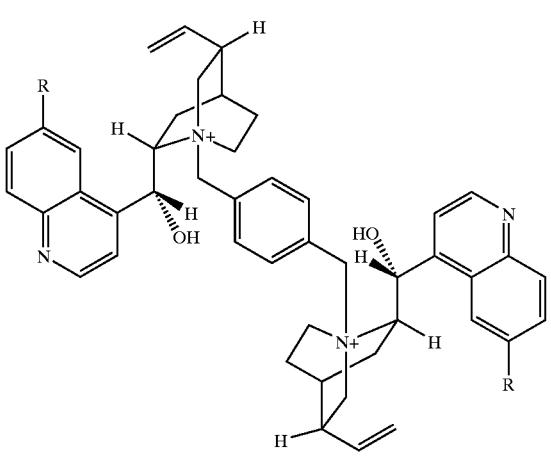

wherein
R represents independently for each occurrence hydroxyl, alkoxyl, or aryloxyl.

Methods of the Invention—Catalyzed Reactions

One aspect of the present invention provides methods for stereoselectively producing compounds with at least one stereogenic center from prochiral starting materials. An advantage of this invention is that enantiomerically enriched products can be synthesized from prochiral or, where the methods are used to achieve a kinetic resolution, racemic reactants. Another advantage is that yield losses associated with the production of an undesired enantiomer can be substantially reduced or eliminated altogether.

In general, the invention features a stereoselective nucleophilic addition to a prochiral sp²-hybridized carbon. Specifically, the methods of the present invention comprise combining a non-racemic, chiral phase transfer catalyst, a compound comprising a prochiral center, a helper nucleophile, and a sterically bulky reagent nucleophile. Under the reaction conditions, the sterically bulky reagent nucleophile stereoselectively attacks the prochiral center, generating an enantiomerically enriched or enantiomerically pure chiral center. The substrate compound comprising a prochiral center will include a prochiral electrophilic atom susceptible to attack by the reagent nucleophile. Suitable substrates include ketones, aldehydes, imines, oximes, enones, enals, enoates, enamines, and enimines. The reaction mixture is maintained under conditions appropriate for the chiral catalyst to catalyze stereoselective addition of the reagent nucleophile to the prochiral electrophilic atom. This reaction can be applied to enantioselective processes as well as diastereoselective processes. It may also be adapted for regioselective reactions. One of ordinary skill in the art of organic synthesis will recognize, and be able to ascertain with no more than routine experimentation, numerous examples of enantioselective reactions, kinetic resolutions, and regioselective reactions which may be catalyzed using the methods of the present invention.

In certain embodiments, the present invention relates to a method of asymmetric phase transfer catalysis, comprising the step of: combining, in a biphasic reaction mixture, a chiral non-racemic phase transfer catalyst, a helper nucleophile, a reactive nucleophile, and a substrate comprising a prochiral atom, under conditions wherein said chiral non-racemic phase transfer catalyst catalyzes a stereoselective addition of said reagent nucleophile to said prochiral atom of said substrate to give a chiral non-racemic product. In certain embodiments, said biphasic mixture comprises an aqueous phase and an organic phase. In certain embodiments, said biphasic mixture comprises a solid phase and an organic phase. In certain embodiments, said chiral non-racemic phase transfer catalyst is enantiomerically pure. In certain embodiments, said chiral non-racemic phase transfer catalyst is a cinchona alkaloid.

In certain embodiments of the methods of the present invention, said chiral non-racemic phase transfer catalyst is selected from the group consisting of:

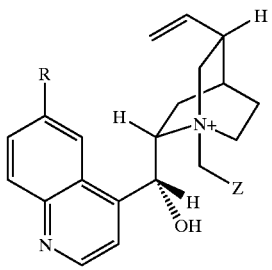

1 wherein
R represents hydroxyl, alkoxyl, or aryloxyl; and
Z represents 9-anthracenyl;

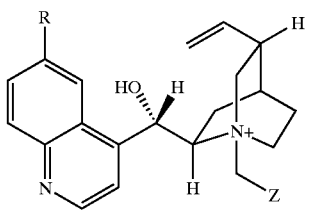

2 wherein
R represents hydroxyl, alkoxyl, or aryloxyl; and
Z represents 9-anthracenyl;

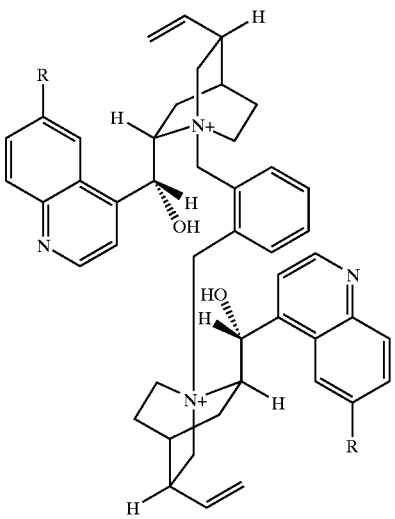

3 wherein
R represents independently for each occurrence hydroxyl, alkoxyl, or aryloxyl;

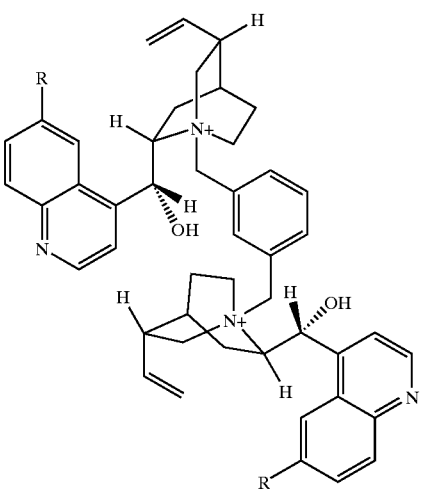

4 wherein
R represents independently for each occurrence hydroxyl, alkoxyl, or aryloxyl; and

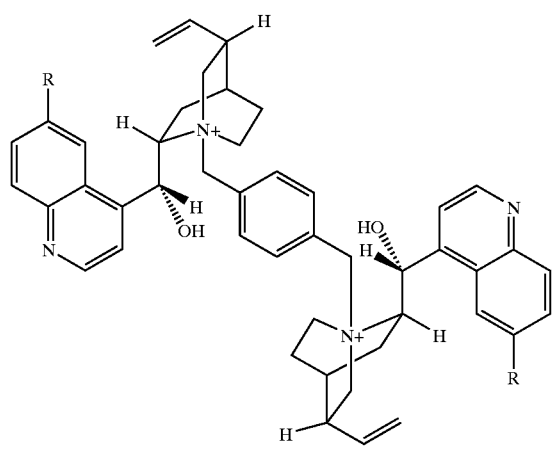

5 wherein
R represents independently for each occurrence hydroxyl, alkoxyl, or aryloxyl.

In certain embodiments of the methods of the present invention, said helper nucleophile is selected from the group consisting of tertiary amines, pyridines, pyrimidines, tertiary phosphines, and tertiary arsines. In certain embodiments, said helper nucleophile is selected from the group consisting of tertiary amines, pyridines, and pyrimidines. In certain embodiments, said helper nucleophile is a pyridine. In certain embodiments, said helper nucleophile is 2-acetylpyridine, 3-acetylpyridine, or 4-acetylpyridine. In certain embodiments, said helper nucleophile is 3-acetylpyridine.

In certain embodiments of the methods of the present invention, said substrate comprising a prochiral atom is selected from the group consisting of ketones, aldehydes, imines, oximes, enones, enals, enoates, enamines, and enimines. In certain embodiments, said substrate comprising a prochiral atom is selected from the group consisting of ketones, aldehydes, imines, oximes, enones, and enals. In certain embodiments, said substrate comprising a prochiral atom is selected from the group consisting of ketones and aldehydes.

In certain embodiments of the methods of the present invention, said reactive nucleophile is selected from the group consisting of hydride, cyanide, enolate anions, malonate anions, and β-ketoester anions. In certain embodiments, said reactive nucleophile is selected from the group consisting of hydride and cyanide. In certain embodiments, said reactive nucleophile is hydride. In certain embodiments, said reactive nucleophile is prepared from a ketone and a hydride reagent.

The processes of this invention can provide optically active products with very high stereoselectivity (e.g., enantioselectivity or diastereoselectivity) or regioselectivity. In preferred embodiments of the subject asymmetric reactions, enantiomeric excesses of preferably greater than about 50%, more preferably greater than about 70%, even more preferably greater than about 80%, and most preferably greater than about 90% can be obtained by the processes of this invention. The processes of this invention can also be carried out under reaction conditions suitable for commercial use, and typically proceed at reaction rates suitable for large scale operations.

As is clear from the above discussion, the chiral products produced by the asymmetric synthesis processes of this invention can undergo further reaction(s) to afford desired derivatives thereof. Such permissible derivatization reactions can be carried out in accordance with conventional procedures known in the art. For example, potential derivatization reactions include esterification, N-alkylation of amides, and the like. The invention expressly contemplates the preparation of end-products and synthetic intermediates which are useful for the preparation or development or both of pharmaceuticals, e.g., cardiovascular drugs, non-steroidal anti-inflammatory drugs, central nervous system agents, and antihistaminics.

Helper Nucleophiles

The addition of a wide range of neutral helper nucleophiles to phase transfer reactions involving chiral non-racemic cationic phase transfer catalysts, an anionic sterically-bulky reagent nucleophile, and a neutral prochiral unsaturated substrate gives increased enantiomeric excesses in the product of the reaction relative to enantiomeric excess in the absence of the neutral nucleophile. This modification has been shown to applicable to the reduction of a prochiral ketone by $NaBH_4$, but should also be applicable to other nucleophilic additions under phase transfer conditions such as reductive amination by $NaCNBH_3$, amino nitrite formation (Strecker amino acid synthesis), Michael additions, nitrite additions; in short, virtually any nucleophilic addition that has been catalyzed under phase transfer conditions.

The possible types of neutral helper nucleophile added are almost limitless, and would be optimized for any given situation. The only limitiation is the requirement that there be no acidic hydrogen directly bonded to the nucleophilic center, so that the addition of the nucleophile to the site of unsaturation in the neutral substrate is reversible. In general, helper nucleophiles useful in the methods of the present invention comprise a Lewis basic atom, e.g., nitrogen, sulfur and phosphorus. For example, aromatic heterocycles comprising a nitrogen atom, e.g., pyridines and pyrimidines, are effective helper nucleophiles in the methods of the present invention. The helper nucleophile need not be chiral.

Reagent Nucleophiles

Reagent nucleophiles which are useful in the present invention may be determined by the skilled artisan according to several criteria. In general, a suitable nucleophile will have one or more of the following properties: 1) It will be capable of reaction with the substrate at the desired electrophilic site; 2) It will yield a useful product upon reaction with the substrate; 3) It will not react with the substrate at functionalities other than the desired electrophilic site; 4) It will react with the substrate at least partly through a mechanism catalyzed by the chiral catalyst; 5) It will not substantially undergo further undesired reaction after reacting with the substrate in the desired sense; and 6) It will not substantially react with or degrade the catalyst. It will be understood that while undesirable side reactions (such as catalyst degradation) may occur, the rates of such reactions can be rendered slow—through the selection of reactants and conditions—in comparison with the rate of the desired reaction(s).

Nucleophiles which satisfy the above criteria can be chosen for each substrate and will vary according to the substrate structure and the desired product. Routine experimentation may be necessary to determine the preferred nucleophile for a given transformation. For example, if a nitrogen-containing nucleophile is desired, it may be selected from ammonia, phthalimide, hydrazine, an amine or the like. Similarly, oxygen nucleophiles such as water, hydroxide, alcohols, alkoxides, siloxanes, carboxylates, or peroxides may be used to introduce oxygen; and mercaptans, thiolates, bisulfite, thiocyanate and the like may be used to introduce a sulfur-containing moiety. Suitable carbon nucleophiles include cyanide, malonate anions, enolates, and β-ketoester anions. Additionally, a wide range of hydride reagents are effective reagent nucleophiles in the methods of the present invention, including sodium borohydride, sodium cyanoborohydride, and sodium triacetoxyborohydride. Additional nucleophiles will be apparent to those of ordinary skill in the art.

In certain embodiments, the reagent nucleophile is sterically bulky. The use of a sterically bulky reagent nucleophile in the phase transfer methods of the present invention frequently generates chiral products with improved enantiomeric excess relative to that obtained with less-hindered anionic reagents. This result has been demonstrated by in situ generation of sterically hindered alkoxyborohydrides from sacrificial ketones in the phase transfer reduction of prochiral ketones, but will likely be applicable with a wide range of generated bulky anionic reagents.

The origin of this effect likely lies in stereodiscriminatory association of the reagent nucleophile anion with the chiral catalyst cation. It has been shown that two sites are available for reagent nucleophile anion binding on a chiral non-racemic catalyst cation used in a model reaction. See Hofstetter, C. et al. *J. Org. Chem.* 1999, 64, 8794–8800. Only one binding mode is expected to result in asymmetric reduction of a substrate, e.g., a prochiral ketone, and steric discrimination by the catalyst between the binding sites results in the observed enhanced enantiomeric excess of the products. See id. By making the anion sterically bulkier, this discrimination becomes greater, thereby improving the enantiomeric excess of the product. See FIG. 3.

The initial counterion of the reagent nucleophile anion can be any of a variety of conventional cations, including alkali and alkaline earth metal cations and ammonium cations. In certain embodiments, the nucleophile may be part of the substrate, thus resulting in an intramolecular reaction.

Substrates

As discussed above, a wide variety of substrates are useful in the methods of the present invention. The choice of substrate will depend on factors such as the nucleophile to be employed and the desired product, and an appropriate substrate will be apparent to the skilled artisan. It will be understood that the substrate preferably will not contain any interfering functionalities. An appropriate substrate will contain at least one reactive, prochiral electrophilic center at which the reagent nucleophile may attack, with the assistance of the chiral non-racemic catalyst and the helper nucleophile. The catalyzed attack of the reagent nucleophile at a prochiral electrophilic center will result in a stereoselective transformation of the substrate.

Most of the substrates contemplated for use in the methods of the present invention contain at least one carbon-heteroatom π-bond. Examples of suitable substrates include ketones, aldehydes, imines, oximes, enones, enals, enoates, enamines, enimines, and the like.

In certain embodiments, the substrate will be a meso compound. In other embodiments, the substrate will be a chiral compound. In certain embodiments, the substrate will be a racemic mixture. In certain embodiments, the substrate will be a mixture of diastereomers. In certain embodiments, the electrophilic atom may be a heteroatom.

Reaction Conditions

The asymmetric reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely effect the substrate, the catalyst, the helper nucleophile, or the product. For example, the reaction temperature influences the speed of the reaction, as well as the stability of the reactants, products, and catalyst. See FIG. 9. The reactions will usually be run at temperatures in the range of −78° C. to 100° C., more preferably in the range −20° C. to 50° C. and still more preferably in the range −20° C. to 25° C.

In general, the asymmetric synthesis reactions of the present invention are carried out in a biphasic reaction mixture, i.e., either liquid-liquid or liquid-solid reaction mixtures. The reactions may be run using a super-critical fluid. Typically, the reactions are run in inert solvents, preferably one of which is water and the other is an inert organic solvent. The aqueous phase of the reaction mixtures may be modified by the addition of a suitable amount of a compound, e.g., a glycol, that depresses its freezing point. Suitable organic solvents are immiscible with water, and include ethers such as diethyl ether, 1,2-dimethoxyethane, diglyme, t-butyl methyl ether, and the like; halogenated solvents such as chloroform, dichloromethane, dichloroethane, chlorobenzene, and the like; aliphatic or aromatic hydrocarbon solvents such as benzene, toluene, hexane, pentane and the like; water-immiscible esters and ketones; or combinations of two or more solvents. Furthermore, in certain embodiments it may be advantageous to employ a solvent which is not inert to the reagent nucleophile under the conditions employed, e.g., the use of the sacrificial ketone as the solvent. In certain embodiments, ethereal solvents are preferred.

The invention expressly contemplates reaction in a biphasic mixture of solvents. Moreover, the present invention contemplates reaction in an emulsion or suspension, or reaction in a lipid vesicle or bilayer. In certain embodiments, it may be preferred to perform the catalyzed reactions in which one phase is the solid phase.

In some preferred embodiments, the reaction may be carried out under an atmosphere of a reactive gas. For example, nucleophilic additions in which cyanide serves as nucleophile may be performed under an atmosphere of HCN gas. The partial pressure of the reactive gas may be from 0.1 to 1000 atmospheres, more preferably from 0.5 to 100 atm, and most preferably from about 1 to about 10 atm.

The asymmetric synthesis processes of the present invention can be conducted in continuous, semi-continuous or batch fashion and may involve a liquid recycle and/or gas recycle operation as desired. The processes of this invention are preferably conducted in batch fashion. Likewise, the manner or order of addition of the reaction ingredients, catalyst and solvent are also not critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone.

The processes may be conducted in glass-lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, the chiral non-racemic catalyst can be immobilized or incorporated into a polymer or other insoluble matrix by, for example, covalently linking it to the polymer or solid support through one or more of its substituents. An immobilized catalyst may be easily recovered after the reaction, for instance, by filtration or centrifugation.

EXEMPLIFICATION

The invention now being generally described, it will be more readily understood by reference to the following examples that are included merely for purposes of illustration of certain aspects and embodiments of the present invention, and are not intended to limit the invention.

EXAMPLE 1

Asymmetric Phase Transfer Reduction of Pirkle's Ketone Using Borohydride

Phase transfer catalysis (PTC) provides a simple and effective means of promoting reaction between water-soluble anions and molecules dissolved in non-polar solvents, such as toluene or chloroform. On an industrial scale, PTC offers considerable economic and environmental benefits: high yields, inexpensive non-toxic catalysts, ease in product isolation, recyclable solvents and reaction at ambient temperatures with no requirement for anaerobic or anhydrous conditions.[1] The use of chiral non-racemic quaternary ammonium ions as phase transfer catalysts can lead to enantiomeric excesses (ee's) in chiral products of PTC reactions. The earliest such observation was made by Balcells et al., who reported modest ee's in the products of the phase transfer $NaBH_4$ reductions of prochiral aryl alkyl ketones when catalyzed by the quinine-derived N-benzyl quininium chloride (NBQCl) 1a.[2a] However, the ee's reported for such reductions were invariably low, probably due to the lack of strong interactions between the neutral organic substrate and the catalytic cation. In contrast, phase transfer alkylations, in which a prochiral anion is generated as an intermediate by deprotonation of the substrate by hydroxide, often exhibit substantial ee's.[3] Presumably, larger ee's are observed in these cases because the direction of approach of the alkylating agent to the prochiral anion is controlled by tight ion pairing between the prochiral anion and the cationic chiral catalyst. The usefulness of chiral PTC would be extended significantly if reactions not involving an anionic prochiral intermediate could also be made to yield products in significant enantiomeric excesses.

[1] Starks, C. M., Liotta, C. L., Halpern, M. *Phase-Transfer Catalysis*, Chapman and Hall, New York, 1994, Ch. 1.
[2] a) Balcells, J. Colonna, S. Fornasier, R. *Synthesis* 1976, 266. b) Julia, S., Ginebreda, A., Guixer, J. Masana, J., Tomas, A., Colonna, S. *J. Chem. Soc., Perkins Trans.* 1984, 1, 574.
[3] (a) O'Donnell et al, *Tetrahedron*, 1994, 50, 4507–4518, (b) Corey, E. J., Xu, F., Noe, M. C. *J. Am. Chem. Soc.* 1997, 119, 12414–12415. (c) Lygo, B., Wainwright, P. G. *Tetrahedron Lett.* 1997, 38, 8595–8598. (d) Lygo, B., Wainwright, P. G. *Tetrahedron Lett.* 1998, 398, 1599–1604. (e) Arai, S., Tsuge, H., Shiori, T. 1998, 39, 7563–7566. (f) Ooi, T., Takeuchi, M., Kameda, M., Maruoka, K. *J. Am. Chem. Soc.* 2000, 122, 5228–5229.

We have used nuclear magnetic resonance (NMR) methods to probe the solution structure and dynamics of ion pairs, particularly those that are involved in phase transfer chemistry.[4] Our analysis[5] of the solution structure of the ion pair formed by N-benzyl quininium with $BH_4^-$(1b) led us to design a catalyst, N-anthryl quininium chloride (NAQCl, 1c), which gave a modest increase in the ee observed in the phase transfer reduction of Pirkle's ketone 2 to the chiral alcohol 3 (Scheme I; Table I).[6] A simple structural and kinetic model has been proposed for the interactions between substrate and ion pair that rationalize the observed sense and extent of ee observed in the model reaction.[7] Other considerations resulting from this model have now led us to modifications that yield further improvements in ee of the model reaction shown in Scheme I.

[4] (a) Pochapsky, T. C., Stone, P. M. *J. Am. Chem. Soc.* 1990, 112, 6714–6715; (b) Stone, P. M., Pochapsky, T. C., Callegari, E., *Chem. Comm.*, 1992, 2, 178–179; (c) Pochapsky, T. C., Wang, A., Stone, P. M. *J. Am. Chem. Soc.*, 1993, 115, 11084–11091; (d) Mo, H., Pochapsky, T. C. *J. Phys. Chem. B*, 1997, 101, 4485–4486. (e) Mo, H., Wang, A., Wilkinson, P. S., Pochapsky, T. C., *J. Am. Chem. Soc.*, 1997, 119, 11666–11673.
[5] Pochapsky, T. C., Pochapsky, S. S., Stone, P. M. *J. Am. Chem. Soc.* 1991, 113, 1460–1462
[6] (a) Stone, P. M., Ph.D. Thesis, Brandeis University, 1993. (b) Mo, H., Pochapsky, T. C. *Prog. NMR Spectrosc.* 1997, 30, 1–38.
[7] Hofstetter, C. H., Wilkinson, P. S., Pochapsky, T. C. *J. Org. Chem.* 1999, 64, 8794–8800.

Scheme I

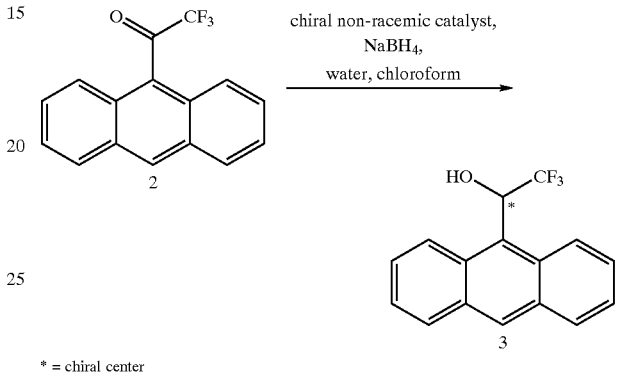

* = chiral center

In the proposed model[7] for the origin of asymmetric induction in the reaction shown in Scheme I, a hydrogen bond between the OH group of the catalyst and the carbonyl oxygen of the substrate ketone 2 is the primary attractive interaction in the reaction complex. It occurred to us that improved ee's in the product alcohol might be obtained if this interaction were strengthened. One way of accomplishing this might be to form a transient zwitterionic species from the substrate ketone by attack at the electrophilic carbon of 2 by a neutral nucleophile such as a tertiary amine or pyridine. This should increase the negative charge density on the oxygen of 2, strengthening the hydrogen bond with the catalyst. In fact, virtually every neutral nucleophile that was tested as a "helper nucleophile" in the model reaction increased ee in the product alcohol 3 to some extent, with pyridine providing the most significant increase (Table I).

[7] Hofstetter, C. H., Wilkinson, P. S., Pochapsky, T. C. *J. Org. Chem.* 1999, 64, 8794–8800.

TABLE I

| Catalyst | Helper nucleophile/sacrificial ketone | % ee |
| --- | --- | --- |
| 1a | none | 20 |
| 1c | none | 30 |
| 1c | Pyridine | 50 |
| 1c | Dibutyl sulfide | 33 |
| 1c | DMAP | 52 |
| 1c | Tributylamine | 34 |
| 1c | Acetone | 40 |
| 1c | Acetophenone | 57 |
| 1c | Benzophenone | 30 |
| 1c | Acetophenone/pyridine | 64 |
| 1c | 4-acetylpyridine | 64 |
| 1c | 2-acetylpyridine | 72 |
| 1c | 3-acetylpyridine | 72/78[a]/86[b] |

Table I presents the results of the reaction shown in Scheme I as a function of helper nucleophile and/or sacrificial ketone. All reactions were performed in 3 ml of $CHCl_3$ using 0.08 mmol of ketone 2, with 10 mol % (0.008 mmol) of catalyst. 2–3 mL of water was added in which was dissolved excess $NaBH_4$. 4 mmol of helper and/or 4 mmol of sacrificial ketone were added per reaction. Reaction were run at room temperature (~22 C) and allowed to go to completion with respect to reduction of 2 unless otherwise noted. Enantiomeric excesses (ee's) were measured by integration of enantiomer peaks resolved via HPLC, using a chiral Regis R-phenylglycine DNB column. Notes: (a) reaction performed at 0° C.; (b) reaction performed at –53 C.

A second important feature of the model is that asymmetric induction occurs at only one of the two $BH_4^-$ binding sites on catalyst 1c that are significantly occupied on a time average.[7] By maximizing the $BH_4^-$ occupation of the site thought to be critical for asymmetric induction (the "OH site" near to the hydroxyl group providing the hydrogen bond to the substrate ketone), the ee should be increased. This was the rationale for the initial design of the catalyst 1c,[6a] and subsequent NMR investigations confirmed that the time-average $BH_4^-$ occupancies of the anion binding sites on 1c are about 2:1 in favor of the "OH site".[7] In the original studies on 1b, the "OH site" is occupied by $BH_4^-$ only half of the time.[5]

[5] Pochapsky, T. C., Pochapsky, S. S., Stone, P. M. *J. Am. Chem. Soc.* 1991, 113, 1460–1462
[6] (a) Stone, P. M., Ph.D. Thesis, Brandeis University, 1993. (b) Mo, H., Pochapsky, T. C. *Prog. NMR Spectrosc.* 1997, 30, 1–38.
[7] Hofstetter, C. H., Wilkinson, P. S., Pochapsky, T. C. *J. Org. Chem.* 1999, 64, 8794–8800.

The basis for the discrimination in $BH_4^-$ binding at the two sites in 1c is steric in nature. The "OH site" (at which asymmetric induction is thought to occur) is less sterically hindered by the anthryl ring of 1c than the second anion binding site (the "V site"), and so can accommodate $BH_4^-$ more easily. It follows that a larger anion than $BH_4^-$ should exhibit even greater discrimination between the two sites of 1c. Such an anion might be generated in situ by reducing a sacrificial ketone RR'C=O to form a borate ester of the form (RR'CHO)$BH_3^-$, which would then act as the reducing agent for ketone 2. Two of the three ketones tested afforded at least some improvement in ee in the model reaction. Acetone did not work as well as acetophenone or any of the acetylpyridines, as expected if it assumed that larger substituents on the borate ester are more effective at providing steric discrimination. However, the sterically largest ketone tried, benzophenone, did not provide any improvement in ee, suggesting that there is a limiting size for providing discrimination in anion binding (Table I). The alcohols formed from the sacrificial ketones had no effect on ee when they were tested separately, indicating that it is the ketone (or the intermediate borate ester formed therefrom) and not the product alcohol that is producing the observed improvement in ee.

The best results to date have been afforded when the two modifications described here (helper nucleophile and sacrificial ketone) are used together, particularly if the helper nucleophile and the sacrificial ketone are combined in the same molecule, e.g., acetylpyridine. This also has the added benefit of making the alcohol produced from the sacrificial ketone easily removed from the reaction mixture by acid extraction. We note in passing that even though chiral alcohols are produced upon reduction of both acetophenone and acetylpyridine, neither exhibits significant ee under the conditions of Scheme I, although this does not rule out preferred binding or reactivity of one diastereomeric ion pair with ketone 2.

These results show that it is possible to considerably increase asymmetric induction for a particular phase transfer reaction even if a strong ion pair between substrate and catalyst is not present in the transition state leading to chiral products. However, an alternate explanation for the observed improvement due to the presence of the helper nucleophile is that small amounts of $BH_3$/pyridine complex are being formed, and that this was the actual reductant. However, the use of reagent $BH_3$/pyridine under PTC conditions with the chiral catalyst present resulted in a racemic product. Moreover, both modifications produce results that are concentration dependent, and preliminary evidence is that a 50-fold excess of both helper nucleophile and sacrificial ketone are required for the best ee's. There does not, however, appear to be any significant dependence of ee on catalyst concentration either with or without the modifications. It is likely that a combinatorial approach to optimization will uncover the best conditions for any particular reaction.

There is no reason why the addition of helper nucleophiles could not improve ee for other nucleophilic additions to prochiral substrates under chiral PTC conditions. Clearly, the usefulness of a sacrificial ketone would be limited to reductions by borohydride and related species. However, the principle of increasing anion size to improve selectivity, along with improved catalyst design for a single preferred anion binding mode could not also be applied more generally to the problem of enantioselectivity in PTC.

References and Notes for Example 1

EXAMPLE 2

Chiral Amplification by an Aromatic Prochiral Ketone in the Borohydride Reduction of 9-Anthryl Trifluoromethyl Ketone Using Liquid-Liquid Phase Transfer Conditions Thus far, phase transfer reactions utilizing chiral catalysts that have given significant enantiomeric excess all have an intermediate prochiral enolate anion which can form a tight ion pair with the catalyst cation.[8] Large ees are observed presumably because the direction of approach of the reagent to the prochiral anion is controlled by tight ion pairing between the prochiral anion and the cationic catalyst. It would extend the usefulness of chiral phase transfer catalysis significantly if reactions not involving a prochiral anionic intermediate could also be made to yield high enantiomeric excesses.

[8] [a] Hughes, D. L., Dolling, U. -H., Ryan, K. M., Schoenwaltd, E. F., Grabowski, E. J. J. *J. Org. Chem.* 1987, 52, 4745–4752, [b] O'Donnell et al, *Tetrahedron*, 1994, 50, 4507–4518, (c) Corey, E. J., Xu, F., Noe, M. C. *J. Am. Chem. Soc.* 1997, 119, 12414–12415. (d) Lygo, B., Wainwright, P. G. *Tetrahedron Lett.* 1997, 38, 8595–8598, (e) Lygo, B., Wainwright, P. G. *Tetrahedron Lett.* 1998, 39, 1599–1602. (f) Arai, S., Tsuge, H., Shiori, T. 1998, 39, 7563–7566. [g] Ooi, T., Takeuchi, M., Kameda, M., Maruoka, K. *J. Am. Chem Soc.*, 2000, 122, 5228–5229.

We have previously obtained modest ees (30%)[9] in the phase transfer catalyzed borohydride reduction of 9-anthryl trifluoromethyl ketone ("ketone 1") using N-anthracenylmethylquininium chloride as a catalyst, and have shown the OH moiety on the catalyst is essential for asymmetric induction.[10] In the published model proposed for the origin of asymmetric induction in the borohydride reduction of ketone 1[11], a hydrogen bond between the OH on the catalyst cation and the carbonyl oxygen of the substrate ketone 1 is the primary attractive interaction in the reaction complex. The comparatively low ee's observed in this reaction are likely to be caused by the inability of the catalyst cation to form a tight ion pair with the neutral substrate. If the environment of the substrate were manipulated such that the substrate could form a zwitterionic species, it would be able to interact to a greater extent with the catalyst cation and improve ees. One way of accomplishing this is by nucleophilic attack on the carbonyl carbon by some neutral, reversible nucleophile such as pyridine or a tertiary amine. This should increase the negative charge on the oxygen, and permit a stronger interaction between catalyst cation and substrate.

[9] Hofstetter, C., Wilkinson, P. S., Pochapsky, T. C., *J. Org. Chem.* 1999, 64, 8794–8800.
[10] Hofstetter, C., Pochapsky, T. C., Unpublished results.
[11] Hofstetter, C., Wilkinson, P. S., Pochapsky, T. C., *J. Org. Chem.* 1999, 64, 8794–8800.

Previously, we had noticed that using quinine itself as a catalyst in the reduction of 9-anthryl trifluoromethyl ketone resulted in product alcohol with an ee of 50%; however, the reaction was only about 10 percent complete. As quinine is not ionic, it is not an effective phase transfer catalyst, so very little borohydride actually makes it into the organic layer to react with the substrate ketone. In order to get the reagent borohydride into the organic layer we ran the reaction with quinine and a phase transfer catalyst. Two reactions were run: The first, in which tetrabutylammonium chloride was used as phase transfer catalyst, gave racemic product. The second, in which a chiral catalyst, N-anthryl quininium chloride was used gave product alcohol with a 34% ee. This is an improvement over the catalyst alone.

A large number of reactions were run using various helper compounds, and a variety of catalysts were tried. Experiments using the borohydride reduction of 9-anthryl trifluoromethyl ketone show that a wide variety of tertiary amines, as well as some other compounds, do in fact increase enantiomeric excess (see FIGS. 4–6). The helper compounds are divided into two groups: helper nucleophiles and sacrificial ketones. It was found that 3-acetyl pyridine, which is both a helper nucleophile and a sacrificial ketone, gave the best results. A 78% ee was obtained at 0° C. when the helper to substrate ratio was 50:1, and N-anthryl quininium chloride was used as a catalyst. Decreasing the temperature further to −54° C. (dry ice/ethanol) increased the ee to 86%.

It is clear from the results we have obtained that there is no single mechanism operating here. We have shown that it is possible to considerably increase asymmetric induction in a reaction with a neutral substrate intermediate using several different catalysts. Other reactions involving neutral intermediates could be run using phase transfer methods that could significantly decrease the cost of enantiomerically pure intermediates to synthetic chemists.

We also report here briefly on several new catalysts based on the theory that a catalyst with C2 symmetry would provide two anion-binding sites with the same chirality. An epoxidation of a cyclic enone with a 63% ee was reported in 1986 using such a catalyst.[12] The catalyst was of the same type as catalyst 5 in this work except cinchonine was used instead of quinine. We also synthesized two other similar catalysts 6 and 7 which are much less sterically hindered than 5. Catalyst 7 by itself gives better ee than N-anthracenylmethyl quininium chloride, 1, in our model reaction (Scheme 5.1) but the ee is not effected by the addition of pyridine. Since the ideal conditions and catalyst must be determined for each reaction individually, these catalysts are still promising, and may be very effective for other chiral phase transfer reactions.

[12] Baba, N. Oda, J., Kawaguchi, M. *Agri. Biol. Chem.*, 1986, 50, 3113–3117.

Specific Phase-Transfer Reactions

In all reactions, reagent grade $CHCl_3$, 9-anthryl trifluoromethyl ketone, and $NaBH_4$ were used without further purification. Optimum results were achieved using 50 equivalents of helper nucleophile or sacrificial ketone to substrate ketone and 10 mole percent catalyst. In a typical reaction 0.022 g (0.08 mmol) ketone 1, 0.004 g (0.008 mmol) NAQCl, and 0.48g (4 mmol) 3-acetylpyridin in $CHCl_3$ (total volume 3 ml) was rapidly stirred with 0.15 g (4 mmol) $NaBH_4$ in 6 ml distilled $H_2O$ until the color of ketone 1 disappeared (approximately an hour). Running the reaction in an ice bath slightly improves ee, and is necessary if reaction is scaled up as the reduction is somewhat exothermic. Enantiomers of 9-anthryl trifluoromethyl ethanol were separated by HPLC on a Regis D-Phenylglycine column with 10% 2-propanol in hexane as the eluent.

3-Pyridyl ethanol was isolated from the reaction mixture by extracting the organic layer twice with 1 M HCl. Saturated $NaHCO_3$ solution was added to the aqueous layer until the pH was around 9, and washed twice with $CH_2Cl_2$. The organic layers were combined and dried over $Na_2SO_4$, and the solvent evaporated under reduced pressure. The alcohol was then stirred in an ice bath in 5 ml $CH_2Cl_2$ and 1.1 equivalents of acetyl chloride added dropwise, and let stir for two hours. 10 ml of distilled water was slowly added, and the organic layer washed twice with saturated $NaHCO_3$ and once with distilled $H_2O$. The enantiomers were separated by gas chromatograpy.

Gas Chromatographic separations were performed on a Hewlett Packard HP 6890 Series gas chromatograph with an FID detector and a 10% permethylated β-cyclodextrin column. The oven temperature was ramped from 85° C.–180° C. at a rate of 10 degrees per minute. The inlet temperature was 250° C., and the detector 300° C. All alcohols were acetylated, and eluted at the following temperatures: 3-pyridyl ethanol, 160; acetophenol, 140; propiophenol, 150; 1-phenyl 2-butanol, 160; and 2,2-dimethylpropiophenol, 163.

Preparation of Diquininium catalysts 5–7. (See FIG. 11 for structures)

α,α'-Diquininium-o-xylene Dibromide, 5

To a 200 ml round bottom flask, 0.3 g (1.1 mmol) α,α'-Dibromo-o-xylene and 0.8 g quinine were added to 50 ml acetonitrile and 15 ml benzene. The solution was stirred for several days until it turned dark orange and a yellow precipitate formed. The yellow solid was suction filtered, washed with acetonitrile, and air dried. MP: 190–200° C. (decomposes). $^1$H NMR (298 K, DMSO-d6, 500 MHz) is very ugly because several exchanging conformations of this sterically hindered compound exist.

α,α'-Diquininium-m-xylene Dibromide, 6

To a 200 ml round bottom flask, 0.3 g (1.1 mmol) α,α'-Dibromo-m-xylene and 0.8 g quinine were added to 50 ml acetonitrile and 15 ml benzene. The solution was stirred overnight, heated on low for several hours, and cooled. An excess of benzene was added and the light pink ppt. filtered by gravity. MP: 200–204° C. (decomposes). $^1$H NMR (298 K, DMSO-d6, 500 MHz) δ8.81 (d, 2 $^1$Hs), 8.06 (s, 1 $^1$H), 8.02 (d, 2 $^1$Hs), 7.86 (d, 2 $^1$Hs), 7.72 (m, 1 $^1$H), 7.49 (dd, 2 $^1$Hs), 7.40 (d, 2 $^1$Hs), 6.69 (d, 2 $^1$Hs), 6.62 (d, 2 $^1$Hs), 5.76 (m, 2 $^1$Hs), 5.56 (d,2 $^1$Hs), 5.10 (d, 2 $^1$Hs), 5.00 (d, 2 $^1$Hs), 4.77 (d, 2 $^1$Hs), 4.25 (m, 2 $^1$Hs), 4.03 (s, 6 $^1$Hs), 3.87 (m, 2 $^1$Hs), 3.68 (m, 2 $^1$Hs), 3,56 (m, 2 $^1$Hs), 2.76 (m, 2 $^1$Hs), 2.23 (m, 2 $^1$Hs), 2.12 (m, 2 $^1$Hs), 2.01 (m, 2 $^1$Hs), 1.81 (br. m., 2 $^1$Hs), 1.47 (m, 2 $^1$Hs).

α,α'-Diquininium-p-xylene Dibromide, 7

To a 200 ml roundbottom flask, 0.5 g (1.9 mmol) α,α'-Dibromo-p-xylene and 1.23 g (3.8 mmol) quinine was added to 60 ml acetonitrile and 10 ml benzene. The mixture was heated (on low) while stirring for several hours until all the quinine dissolved and a yellow ppt. formed. The ppt was suction filtered, washed with acetonitrile, and allowed to air dry. MP 208–212° C. (decomposes). $^1$H NMR (298 K, DMSO-d6, 500 MHz) δ8.81 (d, 2 $^1$Hs), 8.02 (d, 2 $^1$Hs), 7.83 (s, 4 $^1$Hs), 7.76 (d, 2 $^1$Hs), 2,49 (dd, 2 $^1$Hs),7.40 (d, 2 $^1$Hs), 6.67 (d, 2 $^1$Hs), 6.61 (d, 2 $^1$Hs), 5.74 (m, 2 $^1$Hs), 5.48 (d, 2 $^1$Hs), 5.10 (d, 2 $^1$Hs), 4.99 (d, 2 $^1$Hs), 4.78 (d, 2 $^1$Hs), 4.20 (m, 2 $^1$Hs), 4.02 (s, 6 $^1$Hs), 3.84 (m, 2 $^1$Hs), 3.69 (m, 4 $^1$Hs), 3.45 (m, 2 $^1$Hs), 2.84 (m, 2 $^1$Hs), 2.21 (m, 2 $^1$Hs), 2.07 (m, 2 $^1$Hs), 2 $^1$Hs), 1.99 (m, 2 $^1$Hs), 1.90 (br., 2 $^1$Hs), 1.43 (m, 2 $^1$Hs).

Helpers Nucleophiles

FIGS. 4 and 5 list the helper nucleophiles and sacrificial ketones that were tried in the reduction of 9-anthryl trifluoromethyl ketone. Most of the helper nucleophiles first tried increased the ee of the reaction, with pyridine giving the best results. If nucleophilic attack by pyridine at the substrate carbonyl is increasing the electron density on the carbonyl oxygen such that can form a tighter complex with the catalyst cation, then 4-aminopyridine should strengthen this effect.

Scheme 5.1

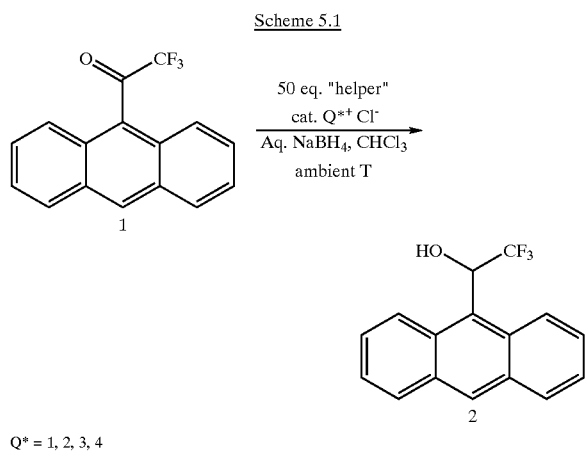

$Q^* = 1, 2, 3, 4$

Figure 6:
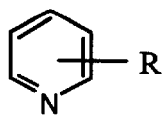
FIG. 6 tabulates the enantiomeic excesses observed using various substituted pyridines as helper nucleophiles in the borohydride reduction of 9-anthryl trifluoromethyl ketone.

FIG. 6 shows the surprising results obtained when various substituted pyridines were used as helper nucleophiles. The substituent has a large effect on the observed ee in the product alcohol, but the position the substituent occupies on the ring does not appear to have much effect on the observed ee. Evidently, the inductive effect alone can not be used to rationalize the results observed, but may still play a role. The more electron rich 4-dimethylaminopyridine (DMAP) when used as a helper nucleophile does give slightly higher ee than pyridine, but aminopyridines as helper nucleophiles give significantly lower ees than pyridine alone. Care needs to be taken when comparing the observed ees presented in FIGS. 4–6 as conditions were not optimized for most of the helpers listed, and optimized conditions could increase ees by more than 10 percent.

It is likely that the mechanims operating in the case of helper nucleophiles and sacrificial ketones are not the same, and, interestingly, the most effective helper is a combination of both groups. One particularly intriguing facet about 3-acetyl pyridine is that it is a prochiral ketone, as is the substrate ketone used in this reaction. It is itself reduced in the process of the reaction, and the resulting 3-pyridyl ethanol is racemic (Scheme 5.3). One proposition, that pyridine or acetyl pyridine could be forming a borane comples in situ (ie. pyridine:BH$_3$) was ruled out. Use of the reagent pyridine:BH$_3$ as the reducing agent with N-anthryl quininium chloride present yielded racemic alcohol 2.

Scheme 5.3

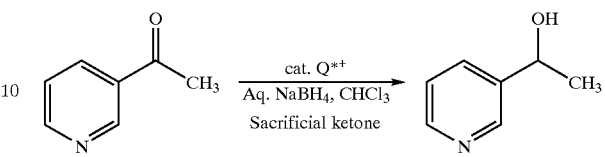

In a previous study[13] we showed that the basis for the discrimination in BH$_4^-$ binding at one of the two accessible sites on the catalyst cation (see FIG. 3) is steric in nature. The site on the catalyst at which asymmetric induction is believed to occur is less sterically hindered by the anthryl ring than the second anion binding site. It follows that a larger anion might have even less accessibility to the more hindered binding site. Such an anion could be created in situ by reducing the sacrificial ketone RR'C=O to form a borate ester of the form (RR'CHO)BH$_3^-$, and it is this species which is reducing ketone 1. Three of the five ketones tested (FIG. 5) afforded some improvement in ee in the model reaction. Acetone did not work as well as the bulkier prochiral ketones, acetophenone and the acetylpyridines, which is expected if the larger substituents on the borate ester lead to a greater steric discrimination. However, neither benzophenone, the sterically largest ketone tried, nor 1-phenyl 2-butanone, provided any improvement in ee, suggesting that there is a limiting size for providing discrimination in anion binding.

[13] Hofstetter, C., Wilkinson, P. S., Pochapsky, T. C., *J. Org. Chem.* 1999, 64, 8794–8800

Another factor that needs to be considered is that the most effective sacrificial ketones are prochiral. It is possible that only one of the borate ester enantiomers interacts strongly with the catalyst cation, or that only one of the diastereomeric ion pairs is reactive toward ketone 1. The reaction is insensitive to the concentration of either catalyst or sodium borohydride, but the ratio of sacrificial ketone to substrate is critical, and reaches a maximum near 50:1 for 3-acetylpyridine (see FIG. 7). A very large excess of sacrificial ketone is needed to produce high ees which further suggests that it is the borate ester that is the reducing species, and that a large excess of borate ester needs to be present to effectively compete with NaBH$_4$. At a substrate to sacrificial ketone ratio of 100:1, the ee is somewhat decreased. It is possible, since the reduction of sacrificial ketone is exothermic, and that this experiment was not carried out in a temperature controlled environment, an increase in temperature is responsible for the diminished ee. It is also possible that as the concentration of borate ester of 2-(3-pyridyl) ethanol is increased, both of these enantiomers become responsible for reducing 9-anthryltrifluoromethyl ketone.

FIG. 8 lists the ees obtained from the model reaction as a function of time. Time zero is the time at which the aqueous NaBH$_4$ solution was added to the reaction mixture. Aliquots of about 5 drops of organic layer were removed from the reaction mixture and quenched. As the reaction proceeds, the ees decrease, lending further support to the hypothesis that some initially formed intermediate species is formed, and that it is this species that is responsible for reducing ketone 1, resulting in an increase in observed ees.

Temperature also effects the observed ees, as the barrier to the activated complex is a function of temperature, and as would be expected, lower temperatures give higher ees (see FIG. 9). An 86% ee was achieved at −60° C. (dry ice ethanol bath). In this last reaction, ethylene glycol was added to the aqueous layer to keep it from freezing. It is not believed that the ethylene glycol has any role other than to keep the water from freezing, but that has not yet been shown.

It is almost certain that the mechanism responsible for the increased enantiomeric excess observed with helper nucleophiles and sacrificial ketones is not the same; however, the most successful "helper" has the properties of both groups in one molecule. Pyridine by itself yields a 50% ee, and acetophenone by itself 57%; when both helper nucleophile and sacrificial ketone are used together, the ee is further increased to 64% (FIG. 10). This is still significantly less than acetylpyridine. Clearly, both the amine nitrogen and the keto group play a role, but their actions in 3-acetyl pyridine are more than a sum of their respective parts.

Other Catalysts

Figure 11:
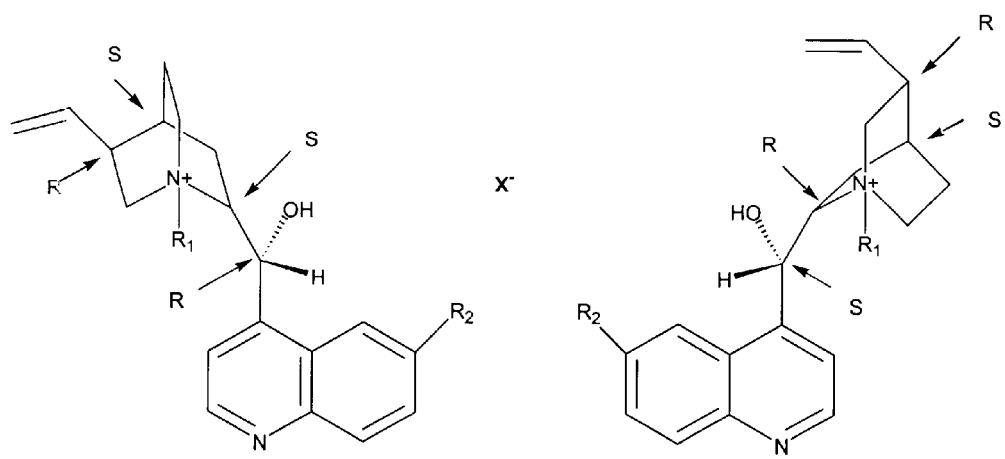
FIG. 11 depicts various phase transfer catalysts to which Example 2 makes reference.
Figure 11:
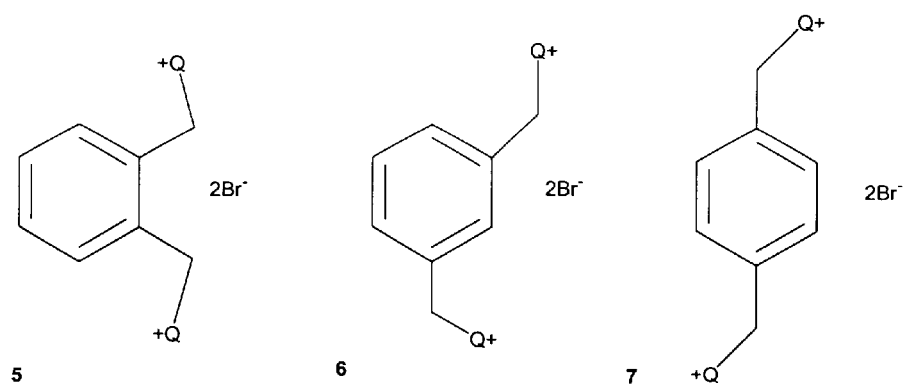

Several other catalysts were tested using our model reaction, several of which are new (see FIG. 11). Note that pseudoenantiomers quinine/quinidine and cinchonidine/cinchonine give opposite enantiomers, and pyridine improves ees in both cases. Interestingly, the ee with the C-2 diquinine catalysts does not appear to be affected by the addition of pyridine; however, catalyst cation 7 is better than catalyst cation 1, which to date, has been the most effective catalyst.

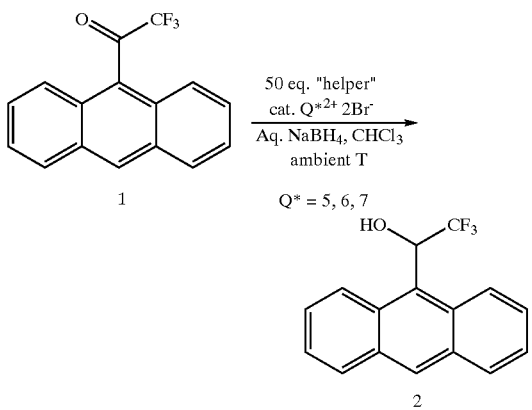

In the comparison of quinine and quinidine based catalysts, they do appear to give nearly equal and opposite ees, further supporting the theory that the binding site near the OH group is, in fact, responsible for the observed asymmetric induction. The cinchonidine based catalysts are definitely more effective than the cinchonine based catalysts suggesting that the anion binding site not responsible for asymmetric induction is less well blocked in cation 4. It is possible that this is not true in the quinidine case because the methoxy group allows only one favorable position of the quinoline ring, and the quinoline ring, as well as the anthryl ring, is partially responsible for blocking the binding site that is not responsible for asymmetric induction. In cations 2 and 4 the OH group is on the side of the molecule away from the quinoline ring making the position of the quinoline ring more critical to the effectiveness of those cations.

Cations 1 and 2 give better asymmetric induction with pyridine present than do cations 3 and 4. Cations 1 and 2 may be able to form large aggregates, whereas cations 3 and 4 do not exhibit this behavior. It is possible that some complex aggregate is responsible for the observed asymmetric induction with quinine and quinidine based catalysts. Further studies to ascertain the extent of aggregation occurring with these ion pairs is of great importance at this time.

It was hoped that the diquininium catalysts (5–7) because of their C-2 symmetry, would afford better ees. Cation 7 does yield slightly higher ees than cation 1 without the presence of helper nucleophile, but the helper nucleophile does not increse the observed ee. The helper nucleophile also has no effect when cation 6 is used. Catalyst cation 5 gave poor ees, so it was not tried with pyridine. In both cations 6 and 7 the two quinine rings are equivalent, so should afford two sets of binding sites. It is difficult to speculate on these results as the lack of solubility of the catalyst cation in sufficiently non-polar media to observe interionic NOEs to $BH_4^-$. It is possible that it is the very limited solubility of the catalysts with cations 5–7 in $CHCl_3$ or $CH_2Cl_2$ that is rendering helper nucleophiles ineffective when used in conduction with them. These diquinium catalysts still are promising and may be very effective in other reactions.

Conclusion

It is possible to use phase transfer catalysis to achieve high enantiomeric excesses in reaction with a neutral intermediate by using a prochiral sacrificial ketone in addition to a chiral catalyst. In the reaction studied here, the product alcohol, 2, is easily separated from the 2-(3-pyridyl) ethanol produced as a by-product, and the 2-(3-pyridyl) ethanol can be isolated and recycled making this an attractive sythesis to industry. Although the use of helper nucleophiles has only been tested in our model reaction (Scheme 5.1), there is no reason, in principle, that the addition of helper nucleophiles could not improve ees for other nucleophilic additions to prochiral substrates under PTC conditions. Of course, the scope of the use of sacrificial ketones is much more limited; however, the underlying implications that increasing anion size to improve selectivity is far reaching. The principle of designing catalysts with a single preferred anion binding mode can also be applied more generally to enantioselective PTC.

References and Notes for Example 2

[8][a]Hughes, D. L., Dolling, U.-H., Ryan, K. M., Schoenwaltd, E. F., Grabowski, E. J. J. J. Org. Chem. 1987, 52, 4745–4752, [b]O'Donnell et al, Tetrahedron, 1994, 50, 4507–4518, (c) Corey, E. J., Xu, F., Noe, M. C. J. Am. Chem. Soc.1997, 119, 12414–12415. (d) Lygo, B., Wainwright, P. G. Tetrahedron Lett. 1997, 38, 8595–8598, (e) Lygo, B., Wainwright, P. G. Tetrahedron Lett. 1998, 39, 1599–1602. (f) Arai, S., Tsuge, Shiori, T. 1998, 39, 7563–7566. [g]Ooi, T., Takeuchi, M., Kameda, M., Maruoka, K. J. Am. Chem Soc., 2000, 122, 5228–5229.
[9]Hofstetter, C., Wilkinson, P. S., Pochapsky, T. C., J. Org. Chem. 1999, 64, 8794–8800.
[10]Hofstetter, C., Pochapsky, T. C., Unpublished results.
[11]Hofstetter, C., Wilkinson, P. S., Pochapsky, T. C., J. Org. Chem. 1999, 64, 8794–8800.
[12]Baba, N. Oda, J., Kawaguchi, M. Agric. Biol. Chem. 1986, 50, 3113–3117.
[13]Hofstetter, C., Wilkinson, P. S., Pochapsky, T. C., J. Org. Chem. 1999, 64, 8794–8800

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are encompassed by the following claims.

We claim:
1. A method of asymmetric phase transfer catalysis, comprising the step of:
combining, in a biphasic reaction mixture, a chiral non-racemic phase transfer catalyst selected from the group consisting of:

1

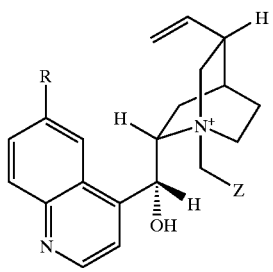

wherein
R represents hydroxyl, alkoxyl, or aryloxyl; and
Z represents 9-anthracenyl;

2

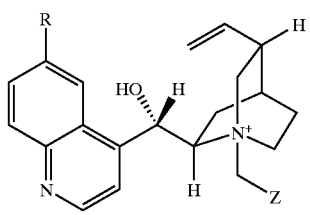

wherein
R represents hydroxyl, alkoxyl, or aryloxyl; and
Z represents 9-anthracenyl;

3

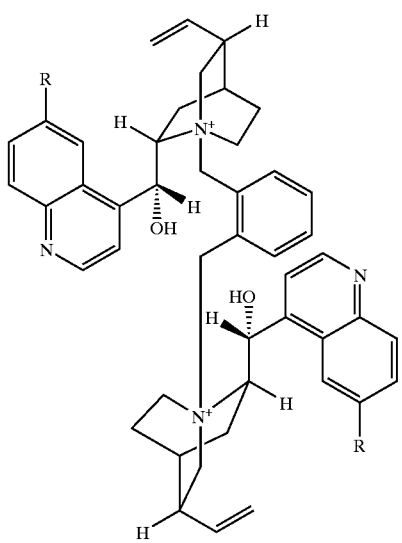

wherein
R represents independently for each occurrence hydroxyl, alkoxyl, or aryloxyl;

4

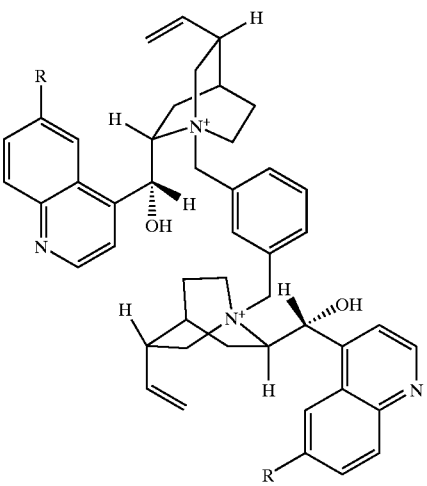

wherein
R represents independently for each occurrence hydroxyl, alkoxyl, or aryloxyl; and

5

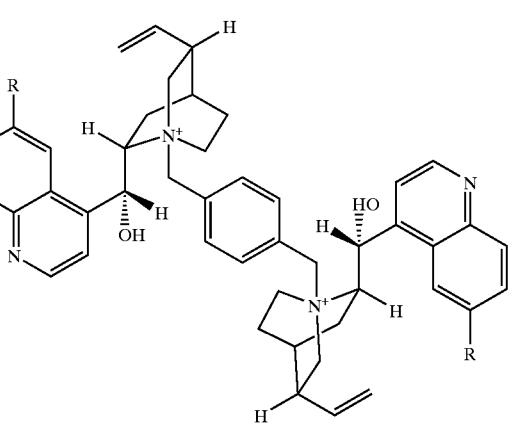

wherein
R represents independently for each occurrence hydroxyl, alkoxyl, or aryloxyl;
a helper nucleophile, a reactive nucleophile, and a substrate comprising a prochiral atom, under conditions wherein said chiral non-racemic phase transfer catalyst catalyzes a stereo selective addition of said reactive nucleophile to said prochiral atom of said substrate to give a chiral non-racemic product.

2. The method of claim 1, wherein said biphasic mixture comprises an aqueous phase and an organic phase.

3. The method of claim 1, wherein said biphasic mixture comprises a solid phase and an organic phase.

4. The method claim 1, wherein said chiral non-racemic phase transfer catalyst is enantiomerically pure.

5. The method claim 1, wherein said helper nucleophile is selected from the group consisting of tertiary amines, pyridines, pyrimidines, tertiary phosphines, and tertiary arsines.

6. The method claim 1, wherein said helper nucleophile is selected from the group consisting of tertiary amines, pyridines, and pyrimidines.

7. The method claim 1, wherein said helper nucleophile is a pyridine.

8. The method of claim 1, wherein said helper nucleophile is 2-acetylpyridine, 3-acetylpyridine, or 4-acetylpyridine.

9. The method of claim 1, wherein said helper nucleophile is 3-acetylpyridine.

10. The method of claim 1, wherein said substrate comprising a prochiral atom is selected from the group consisting of ketones, aldehydes, imines, oximes, enones, enals, enoates, enamines, and enimines.

11. The method of claim 1, wherein said substrate comprising a prochiral atom is selected from the group consisting of ketones, aldehydes, imines, oximes, enones, and enals.

12. The method of claim 1, wherein said substrate comprising a prochiral atom is selected from the group consisting of ketones and aldehydes.

13. The method of claim 1, wherein said reactive nucleophile is selected from the group consisting of hydride, cyanide, enolate anions, malonate anions, and β-ketoester anions.

14. The method of claim 1, wherein said reactive nucleophile is selected from the group consisting of hydride and cyanide.

15. The method of claim 1, wherein said reactive nucleophile is hydride.

16. The method of claim 1, wherein said reactive nucleophile is prepared from a ketone and a hydride reagent.

17. The method of claim 1, wherein the substrate is a racemic or diastereomeric mixture; and said method results in a kinetic resolution of the substrate.

18. The method of claim 1, wherein the chiral non-racemic product has an enantiomeric excess greater than about 50%.

19. The method of claim 1, wherein the chiral non-racemic product has an enantiomeric excess greater than about 70%.

20. The method of claim 1, wherein the chiral non-racemic product has an enantiomeric excess greater than about 80%.

21. A compound represented by structure 3:

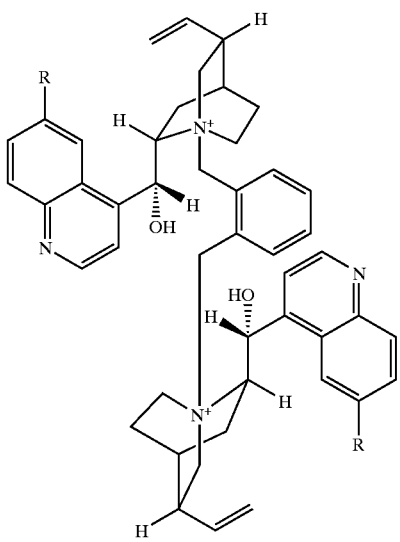

3 wherein
R represents independently for each occurrence hydroxyl, alkoxyl, or aryloxyl.

22. A compound represented by structure 4:

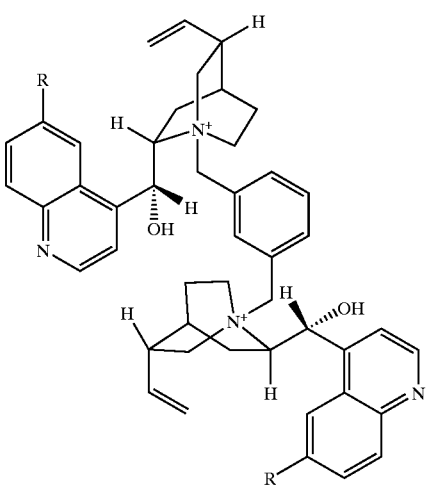

4 wherein
R represents independently for each occurrence hydroxyl, alkoxyl, or aryloxyl.

23. A compound represented by structure 5:

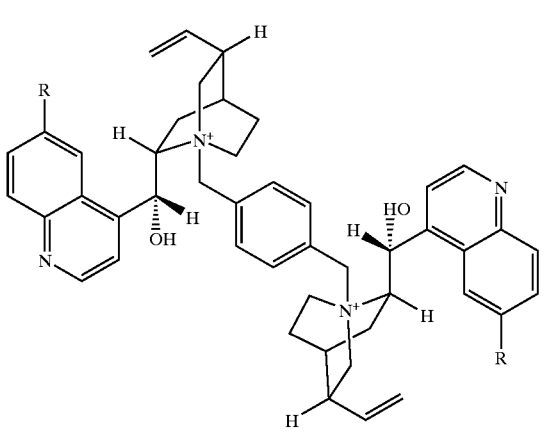

5 wherein
R represents independently for each occurrence hydroxyl, alkoxyl, or aryloxyl.

24. The method claim 1, wherein said helper nucleophile is a pyridine; said substrate comprising a prochiral atom is selected from the group consisting of ketones, aldehydes, imines, oximes, enones, enals, enoates, enamines, and enimines; and said reactive nucleophile is selected from the group consisting of hydride and cyanide.

25. The method of claim 1, wherein said helper nucleophile is 2-acetylpyridine, 3-acetylpyridine, or 4-acetylpyridine; said substrate comprising a prochiral atom is selected from the group consisting of ketones, aldehydes, imines, oximes, enones, and enals; and said reactive nucleophile is hydride.

26. The method of claim 1, wherein said helper nucleophile is 3-acetylpyridine; said substrate comprising a prochiral atom is selected from the group consisting of ketones and aldehydes; and said reactive nucleophile is prepared from a ketone and a hydride reagent.

27. The method of claim 24, 25, 26, wherein the substrate is a racemic or diastereomeric mixture; and said method results in a kinetic resolution of the substrate.

* * * * *